US011382600B2

(12) United States Patent
Taniguchi

(10) Patent No.: US 11,382,600 B2
(45) Date of Patent: *Jul. 12, 2022

(54) ULTRASOUND DIAGNOSTIC IMAGING APPARATUS

(71) Applicant: KONICA MINOLTA, INC., Tokyo (JP)

(72) Inventor: Tetsuya Taniguchi, Hachioji (JP)

(73) Assignee: KONICA MINOLTA INC., Tokyo (JP)

( * ) Notice: Subject to any disclaimer, the term of this patent is extended or adjusted under 35 U.S.C. 154(b) by 1025 days.

This patent is subject to a terminal disclaimer.

(21) Appl. No.: 16/025,413

(22) Filed: Jul. 2, 2018

(65) Prior Publication Data

US 2018/0303455 A1    Oct. 25, 2018

Related U.S. Application Data

(63) Continuation of application No. 14/194,124, filed on Feb. 28, 2014, now Pat. No. 10,912,535.

(30) Foreign Application Priority Data

Mar. 4, 2013 (JP) ................................. 2013-041380

(51) Int. Cl.
*A61B 8/00* (2006.01)
*A61B 8/14* (2006.01)
(Continued)

(52) U.S. Cl.
CPC .................. *A61B 8/14* (2013.01); *A61B 8/54* (2013.01); *G01S 7/5202* (2013.01);
(Continued)

(58) Field of Classification Search
CPC ..................................... A61B 8/14; A61B 8/15
See application file for complete search history.

(56) References Cited

U.S. PATENT DOCUMENTS 6,193,659 B1    2/2001   Ramamurthy et al.
7,022,074 B2    4/2006   Kristoffersen et al.
(Continued)

FOREIGN PATENT DOCUMENTS

JP    2005000663 A    1/2005
JP    2006087745 A    4/2006
(Continued)

OTHER PUBLICATIONS

Japanese Office Action dated Jan. 8, 2019 (and English translation thereof) issued in Japanese Application No. 2018-019823.
(Continued)

*Primary Examiner* — Rajeev P Siripurapu
(74) *Attorney, Agent, or Firm* — Holtz, Holtz & Volek PC

(57) ABSTRACT

An ultrasound diagnostic apparatus including an ultrasound probe which outputs transmission ultrasound corresponding to a drive signal, which receives reflected ultrasound from the subject and which outputs a received signal according to the reflected ultrasound; a drive signal outputter which outputs the drive signal to the ultrasound probe; a hardware processor which controls the drive signal outputter to output a first drive signal having a first drive waveform and a second drive signal having a second drive waveform that is different from the first drive waveform; a received signal generator which generates a first received signal based on the reflected ultrasound corresponding to the transmission ultrasound that is output based on the first drive signal and a second received signal based on the reflected ultrasound corresponding to the transmission ultrasound that is output based on the second drive signal; and an extractor which extracts by arithmetic of the first received signal and the second received signal a received signal component which to be used in imaging. Frequency spectrums of the first drive signal and the second drive signal have a first intensity peak
(Continued)

on a low frequency side of a center frequency of the transmission frequency, a second intensity peak on a high frequency side of the center frequency and a third intensity peak at a frequency between a frequency corresponding to the first intensity peak and a frequency corresponding to the second intensity peak, in a frequency band included in a transmission frequency band at −20 dB of the ultrasound probe.

6 Claims, 17 Drawing Sheets

(51) Int. Cl.
    *G01S 7/52*     (2006.01)
    *G01S 15/89*     (2006.01)
    *A61B 8/15*     (2006.01)
    *A61B 8/08*     (2006.01)

(52) U.S. Cl.
    CPC ........ *G01S 7/52038* (2013.01); *G01S 15/895* (2013.01); *A61B 8/15* (2013.01); *A61B 8/4405* (2013.01); *A61B 8/5207* (2013.01)

(56) References Cited

U.S. PATENT DOCUMENTS

| | | | |
|---|---|---|---|
| 7,713,199 B2 | 5/2010 | Mo et al. | |
| 8,480,586 B2 | 7/2013 | Tsao et al. | |
| 2003/0013969 A1 | 1/2003 | Erikson et al. | |
| 2003/0060712 A1* | 3/2003 | Kawagishi | G01S 7/52038 600/443 |
| 2004/0039283 A1 | 2/2004 | Banjanin et al. | |
| 2004/0254459 A1 | 12/2004 | Kristoffersen et al. | |
| 2006/0079779 A1 | 4/2006 | Takimoto | |
| 2007/0055160 A1 | 3/2007 | Ng et al. | |
| 2008/0249417 A1* | 10/2008 | Averkiou | A61B 8/00 600/459 |
| 2008/0275338 A1 | 11/2008 | Jensen et al. | |
| 2012/0310091 A1 | 12/2012 | Ohnuma et al. | |
| 2013/0006113 A1 | 1/2013 | Taniguchi | |

FOREIGN PATENT DOCUMENTS

| | | |
|---|---|---|
| JP | 2006340886 A | 12/2006 |
| JP | 2007029745 A | 2/2007 |
| JP | 2007510450 A | 4/2007 |
| JP | 2008043721 A | 2/2008 |
| JP | 2012245307 A | 12/2012 |
| WO | 2005043188 A1 | 5/2005 |
| WO | 2011114852 A1 | 9/2011 |

OTHER PUBLICATIONS

Office Action (Examiner's Answer to Appeal Brief) dated Nov. 29, 2018 issued in U.S. Appl. No. 14/194,124.

Japanese Office Action (and English translation thereof) dated Jan. 19, 2016, issued in counterpart Japanese Application No. 2013-041380.

Japanese Office Action (and English translation thereof) dated May 9, 2017, issued in counterpart Japanese Application No. 2013-041380.

Japanese Office Action (and English translation thereof) dated Sep. 6, 2016, issued in counterpart Japanese Application No. 2013-041380.

Japanese Office Action dated Nov. 7, 2017 issued in counterpart Japanese Application No. 2013-041380.

* cited by examiner

ULTRASOUND DIAGNOSTIC IMAGING APPARATUS

CROSS-REFERENCE TO RELATED APPLICATIONS

This is a Continuation of U.S. application Ser. No. 14/194,124, filed Feb. 28, 2014, which is based upon and claims the benefit of priority from prior Japanese Patent Application No. 2013-041380, filed Mar. 4, 2013, the entire contents of both of which are incorporated herein by reference.

BACKGROUND OF THE INVENTION

1. Field of the Invention

The present invention relates to an ultrasound diagnostic imaging apparatus.

2. Description of Related Art

In a conventional ultrasound diagnostic imaging apparatus, an ultrasound probe transmits ultrasound (transmission ultrasound) to a subject such as a living body and the ultrasound probe converts the received ultrasound (reflected ultrasound) into received signals to display an ultrasound image based on the received signals. Since the reflected ultrasound includes information which indicates the condition inside the subject, it is important to obtain good reflected ultrasound in order to obtain an ultrasound image of good quality. Although the image quality of an ultrasound image can be improved by performing signal processing on the received signals, it is essentially desired that the transmission ultrasound has good quality.

Transmission ultrasound having good quality means having good resolution. In order to realize high resolution, it is required that the transmission ultrasound has short pulse widths. By making the frequency band of the transmission ultrasound be a broad band or by making the frequency of the transmission ultrasound be a high-frequency, short pulses can be realized.

In view of the above, for example, JP 2008-43721 discloses that the waveform of a transmission signal is arbitrarily adjusted in order to obtain the desired transmission ultrasound waveform in a conventional ultrasound diagnostic imaging apparatus.

SUMMARY OF THE INVENTION

However, in the technique described in JP 2008-43721, in order to obtain an ultrasound image of high resolution, a highly accurate and expensive transmission drive apparatus which can form an arbitrary waveform and control the waveform formation using a circuit is required. On the other hand, since such expensive transmission drive apparatus cannot be used in a small and low-cost ultrasound diagnostic imaging apparatus, there is no choice but to compromise on image quality.

In view of the above circumstances, an object of the present invention is to provide an ultrasound diagnostic imaging apparatus which can maintain high resolution while keeping the cost down.

In order to realize at least one of the above objects, an ultrasound diagnostic imaging apparatus reflecting one aspect of the present invention includes an ultrasound probe which outputs transmission ultrasound toward a subject due to a pulse signal being input and which outputs a received signal by receiving reflected ultrasound from the subject, and a transmission unit which makes the ultrasound probe generate the transmission ultrasound by outputting a pulse signal whose drive waveform is formed of rectangular waves, and a frequency power spectrum of the pulse signal has intensity peaks in a frequency band included in a transmission frequency band at −20 dB of the ultrasound probe on a low frequency side and a high frequency side of a center frequency of the transmission frequency band, respectively, and intensity of a frequency region between the intensity peaks is −20 dB or greater with a maximum value of intensity among the intensity peaks being a reference.

Preferably, the transmission unit outputs pulse signals of different drive waveforms on a same scanning line for a plurality of times with a time interval therebetween, and the ultrasound diagnostic imaging apparatus further includes an image generation unit which combines received signals each of which obtained from the reflected ultrasound of the transmission ultrasound generated by each output of pulse signal and generates ultrasound image data on a basis of a composite pulse signal.

Preferably, in the frequency power spectrum of the pulse signal, intensity of a frequency component at at least one intensity peak among the intensity peaks is greater than intensity of a frequency component at a frequency same as the center frequency in the transmission frequency band at −20 dB of the ultrasound probe.

Preferably, the frequency power spectrum of the pulse signal includes two or more intensity peaks in the transmission frequency band on the high frequency side of the center frequency of the transmission frequency band at −20 dB of the ultrasound probe.

Preferably, the pulse signal is formed of rectangular waves of five values or less.

Preferably, in the ultrasound probe, a fractional bandwidth at −20 dB is 110% or greater.

BRIEF DESCRIPTION OF THE DRAWINGS

The present invention will become more fully understood from the detailed description given hereinbelow and the appended drawings which are given byway of illustration only, and thus are not intended as a definition of the limits of the present invention, and wherein.

DESCRIPTION OF THE PREFERRED EMBODIMENTS

Figure 1:
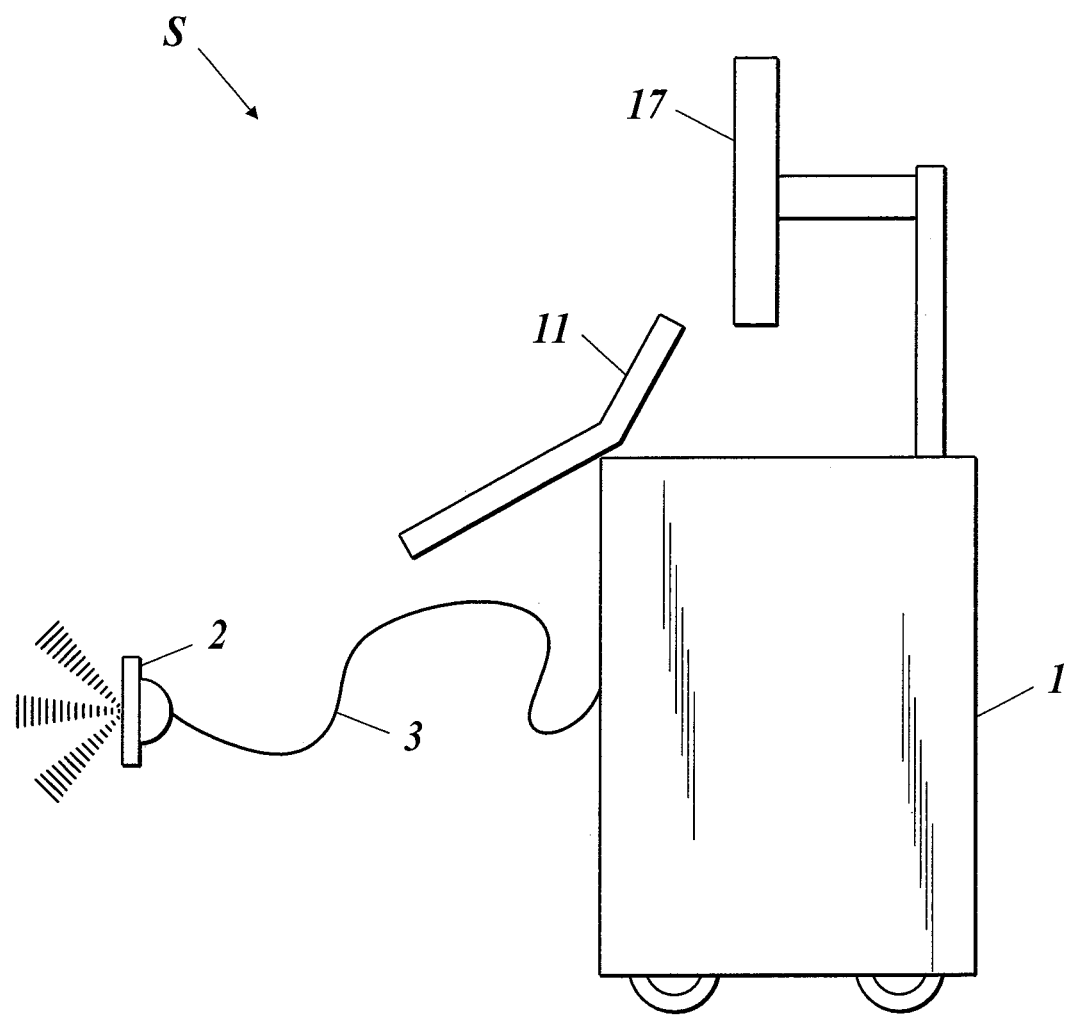
FIG. 1 is a drawing showing an outer structure of an ultrasound diagnostic imaging apparatus.

Hereinafter, the ultrasound diagnostic imaging apparatus according to an embodiment of the present invention will be described with reference to the drawings. However, the scope of the invention is not limited to the examples shown in the drawings. In the following description, same numeral references are used for similar functions and similar configurations and their descriptions are omitted.

Figure 2:
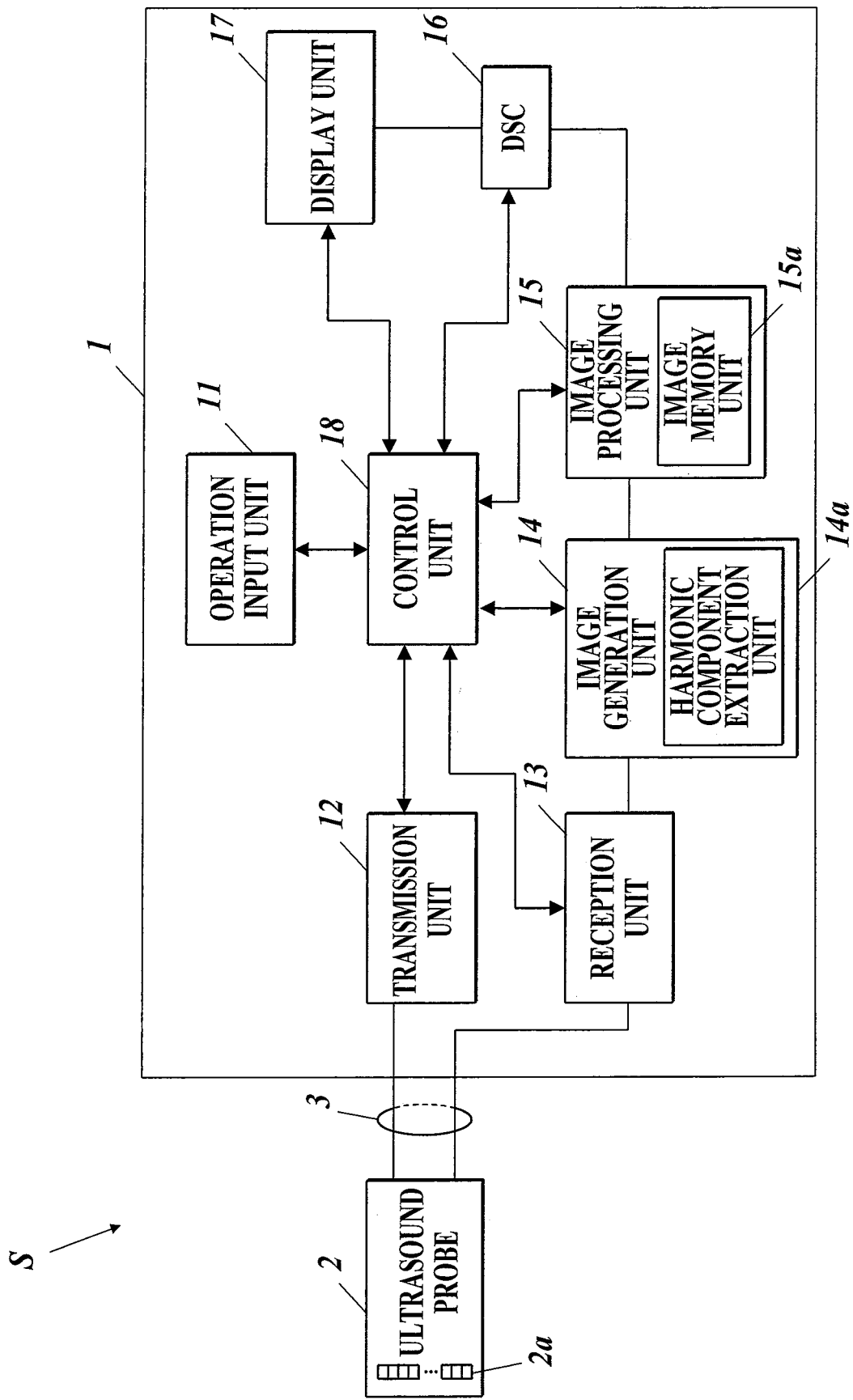
FIG. 2 is a block diagram showing a schematic configuration of the ultrasound diagnostic imaging apparatus.

As shown in FIGS. 1 and 2, the ultrasound diagnostic imaging apparatus S according to an embodiment includes an ultrasound diagnostic imaging apparatus main body 1 and an ultrasound probe 2. The ultrasound probe 2 transmits ultrasound (transmission ultrasound) to a subject such as a living body (not shown in the drawing) and receives reflected wave (reflected ultrasound: echo) of the ultrasound reflected off the subject. The ultrasound diagnostic imaging apparatus main body 1 is connected with the ultrasound probe 2 via a cable 3. The ultrasound diagnostic imaging apparatus main body 1 transmits drive signals which are electric signals to the ultrasound probe 2 to make the ultrasound probe 2 transmit transmission ultrasound to a subject and visualizes the inside state of the subject as an ultrasound image on the basis of the received signals which are electric signals generated in the ultrasound probe 2 according to the reflected ultrasound from inside of the subject received by the ultrasound probe 2.

The ultrasound probe 2 includes transducers 2a formed of piezoelectric elements and for example, the transducers 2a are aligned in a one-dimensional array in an orientation direction. In the embodiment, for example, an ultrasound probe 2 provided with 192 transducers 2a is used. Here, the transducers 2a may be aligned in a two-dimensional array. Further, the number of transducers 2a can be set arbitrarily. Although a linear scanning type electronic-scanning probe is used as the ultrasound probe 2 in the embodiment, either an electronic-scanning type or a mechanic-scanning type can be used. Further, any type of linear scanning, sector scanning and convex scanning can be adopted. In the embodiment, the transmission ultrasound having high resolution can be efficiently obtained by using an ultrasound probe which can transmit ultrasound in a broad band with good sensitivity, and an even better ultrasound image can be obtained. The bandwidth of the ultrasound probe can be set arbitrarily; however, it is preferred that the fractional bandwidth at −20 dB is 110% or greater.

As shown in FIG. 2, the ultrasound diagnostic imaging apparatus main body 1 includes an operation input unit 11, a transmission unit 12, a reception unit 13, an image generation unit 14, an image processing unit 15, a DSC (Digital Scan Converter) 16, a display unit 17 and a control unit 18, for example.

The operation input unit 11 includes various types of switches, buttons, a track ball, a mouse, a key board and the like for inputting commands for instructing the start of diagnosis and data such as personal information relating to a subject, etc. and the operation input unit 11 outputs operation signals to the control unit 18.

Figure 3:
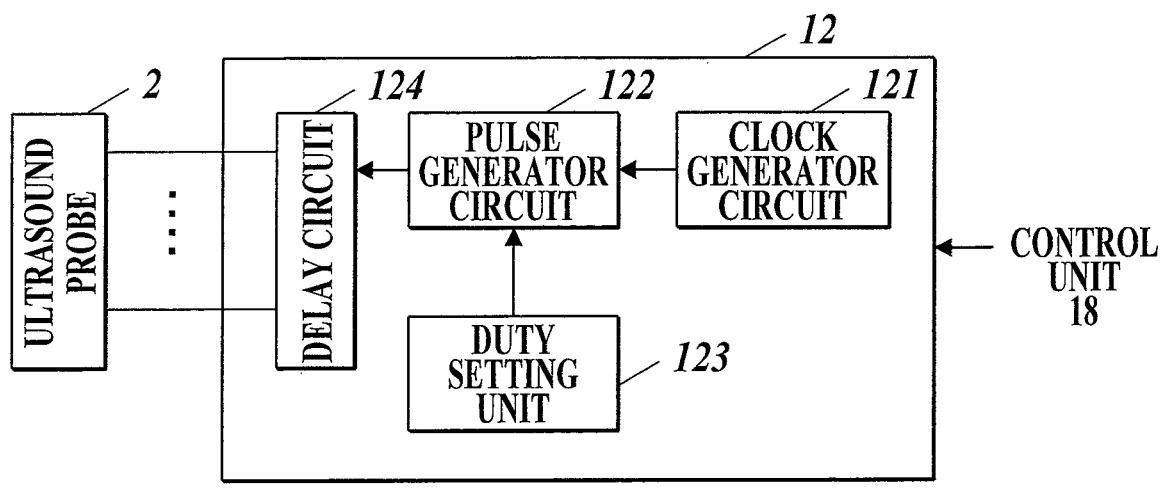
FIG. 3 is a block diagram showing a schematic configuration of a transmission unit.

The transmission unit 12 is a circuit for supplying drive signals which are electric signals to the ultrasound probe 2 via the cable 3 according to the control of the control unit 18 to make the ultrasound probe 2 generate transmission ultrasound. More specifically, as shown in FIG. 3, the transmission unit 12 includes a clock generator circuit 121, a pulse generator circuit 122, a duty setting unit 123 and a delay circuit 124, for example.

The clock generator circuit 121 is a circuit for generating a clock signal for deciding the transmission timing and the transmission frequency of a drive signal.

Figure 4:
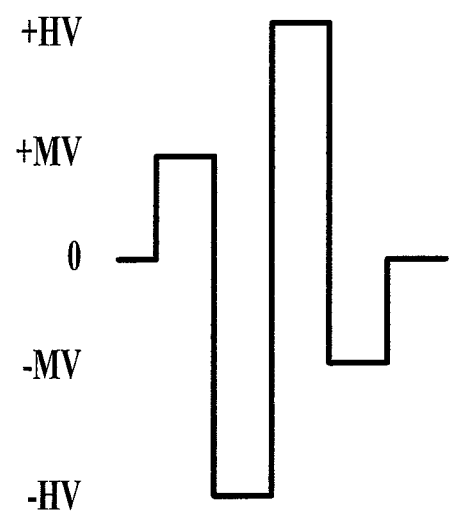
FIG. 4 is a drawing for explaining a drive waveform of a pulse signal.

The pulse generator circuit 122 is a circuit for generating a pulse signal as a drive signal in a predetermined cycle. The pulse generator circuit 122 can generate a pulse signal of rectangular waves by switching between 5 values of voltage (+HV/+MV/0/−MV/−HV) and output the voltage as shown in FIG. 4, for example. Here, the amplitude of the pulse signal is made so as to be the same in the positive polarity and in the negative polarity. However, this is not limitative in any way. In the embodiment, a pulse signal is output by switching among five voltage values. However, the voltage values are not limited to five values and can be set to arbitrary number of values, although, the number of values is desired to be five values or less. In such way, the degree of freedom for controlling the frequency components can be improved at a low cost and transmission ultrasound having even higher resolution can be obtained.

The duty setting unit 123 sets the duty ratio of a pulse signal which is output from the pulse generator circuit 122. That is, the pulse generator circuit 122 outputs a pulse signal of a pulse waveform according to the duty ratio set by the duty setting unit 123. The duty ratio can be changed by the input operation performed on the operation input unit 11.

In the embodiment, the duty setting unit 123 sets the duty ratio of a pulse signal so that a peak included in the transmission frequency band of the ultrasound probe 2 is generated in each of the low frequency side and the high frequency side of the center frequency of the transmission frequency band of the ultrasound probe 2. At this time, the duty setting unit 123 sets the duty ratio of the pulse signal so that the sensitivity of the ultrasound probe at the transmission frequency band of −20 dB be −20 dB or greater.

Figure 5A:
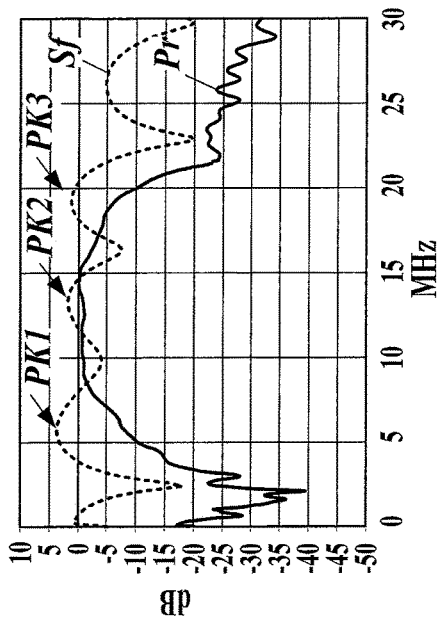
FIG. 5A is a drawing for explaining an example of a transmission bandwidth shape of an ultrasound probe.
Figure 5C:
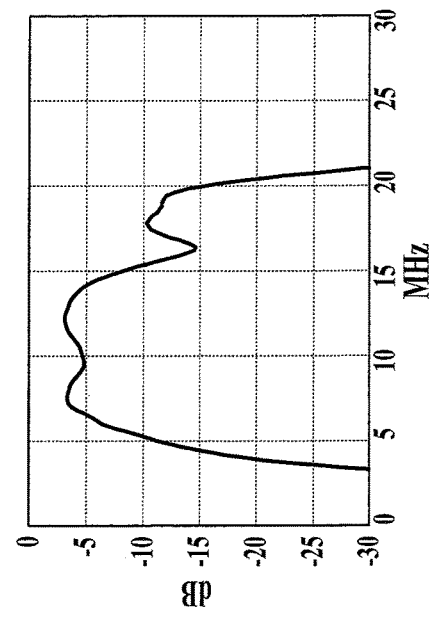
FIG. 5C is a drawing showing frequency power spectrum obtained by performing frequency analysis on the pulse signal shown in FIG. 5B.
Figure 5B:
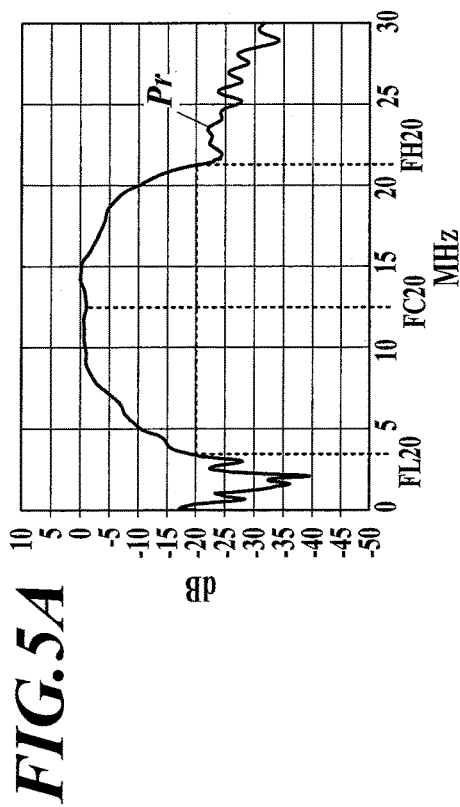
FIG. 5B is a drawing for explaining an example of a drive waveform of a pulse signal which is output from the transmission unit.
Figure 5D:
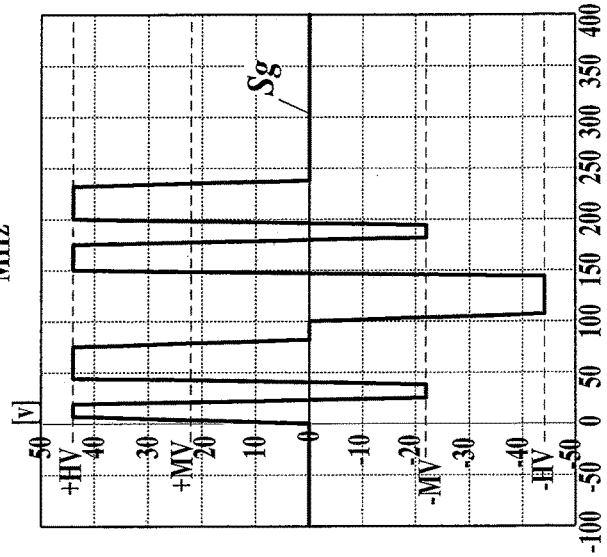
FIG. 5D is a drawing showing a result of frequency analysis performed on transmission ultrasound which is output from the ultrasound probe.

Here, more details will be described with reference to FIG. 5. FIG. 5A shows an example of a transmission bandwidth shape Pr of the ultrasound probe 2. FIG. 5B shows an example of a drive waveform of a pulse signal which is output from the transmission unit 12. FIG. 5C shows a frequency power spectrum obtained by performing frequency analysis (FFT) on the pulse signal shown in FIG. 5B. FIG. 5D shows the result of performing the frequency analysis (FFT) on the transmission ultrasound output from the ultrasound probe 2.

For example, with respect to the ultrasound probe 2 as shown in FIG. 5A, the peak frequency is 14.2 MH, the minimum frequency (FL20) at −20 dB is 3.4 MHz, the maximum frequency (FH20) at −20 dB is 21.2 MHz, the center frequency (FC20) is 12.3 MHz and the fractional bandwidth at −20 db is 145%.

To such ultrasound probe 2, a pulse signal Sg having a drive waveform as shown in FIG. 5B is applied, for example. The pulse signal Sg is formed of rectangular waves and can be generated by switching between five voltage values. The frequency power spectrum obtained by performing the frequency analysis on the pulse signal Sg has, as shown in FIG. 5C, one intensity peak (PK1: 5.8 MHz) on the low frequency side of the center frequency (FC20) in the transmission frequency band at −20 dB of the ultrasound probe 2 and has two intensity peaks (PK2: 13.2 MHz, PK3: 19.2 MHz) on the high frequency side (here, Sf in FIG. 5C shows the analysis result). That is, if a pulse signal having the drive waveform as shown in FIG. 5B is applied to the ultrasound probe 2 having the characteristics as shown in FIG. 5A, the peaks (PK1 to PK3) included in the transmission frequency band of the ultrasound probe 2 are generated on the low frequency side and on the high frequency side of the center frequency (FC20) in the transmission frequency band (FL20-FH20) of the ultrasound probe 2. Intensities at the intensity peaks (P1: 3.8 dB, P2: 2.0 dB, P3: 1.4 dB) are greater than the intensity (1.1 dB) of the frequency component at the frequency (12.3 MHz) which is the same as the center frequency of the transmission frequency band of the ultrasound probe 2. Further, the intensities between the intensity peaks are −20 dB or greater with the intensity at PK1, which is the maximum intensity value among the intensity peaks, being the reference. As a result, the transmission ultrasound having the characteristics as shown in FIG. 5D is output from the ultrasound probe 2.

The transmission bandwidth shape of the ultrasound probe 2 and the drive waveform of the pulse signal in the embodiment is not limitative in any way and can be arbitrarily set within a feasible range.

Further, although all of the plurality of intensity peaks in the pulse signal are greater than the intensity of the frequency component at the frequency which is the same as the center frequency of the transmission frequency band of the ultrasound probe 2 in the embodiment, it is sufficient that at least one or more of the intensity peaks is greater than the intensity of the frequency component at the frequency which is the same as the center frequency of the transmission frequency band of the ultrasound probe 2.

Furthermore, although a pulse signal which gives two intensity peaks on the high frequency side of the center frequency (FC20) in the transmission frequency band of the ultrasound probe 2 is output in the embodiment, there may be three or more of such intensity peaks. When a pulse signal which gives two or more intensity peaks on the high frequency side of the center frequency (FC20) in the transmission frequency band of the ultrasound probe 2 is used, a pulse signal having even broader bandwidth on the high frequency side can be output. A pulse signal which gives only one intensity peak on the high frequency side of the center frequency (FC20) in the transmission frequency band of the ultrasound probe 2 may also be used.

The delay circuit 124 is a circuit for setting delay times in transmission timings of drive signals for individual paths corresponding to the transducers and delays the transmission of the drive signals for the set delay times to concentrate the transmission beams constituted of transmission ultrasound.

The transmission unit 12 configured as described above sequentially switches the transducer 2a which supplies a drive signal among the plurality of transducers 2a by a predetermined number of transducers 2a for every transmission and reception of ultrasound according to the control of the control unit 18 and supplies drive signals to the selected plurality of transducers 2a to perform scanning.

In the embodiment, pulse inversion can be performed in order to extract the after-mentioned harmonic component. That is, when performing pulse inversion, the transmission unit 12 can transmit the first pulse signal and the second pulse signal whose polarity is inverse of that of the first pulse signal on the same scanning line with some time interval therebetween. At this time, the second pulse signal formed by changing at least one of the plurality of duties of the first pulse signal to inverse its polarity may be transmitted. Further, the second pulse signal may be a signal formed by performing time inversion on the first pulse signal.

The reception unit 13 is a circuit for receiving received signals which are electric signals from the ultrasound probe 2 via the cable 3 in compliance with the control of the control unit 18. The reception unit 13 is provided with an amplifier, an A/D conversion circuit and a phasing addition circuit, for example. The amplifier is a circuit for amplifying the received signals at a preset amplification factor for the individual paths corresponding to the transducers 2a. The A/D conversion circuit is a circuit for performing analog/digital conversion (A/D conversion) of the amplified received signals. The phasing addition circuit is a circuit for adjusting time phases of the received signals to which A/D conversion is performed by applying the delay timed to the individual paths respectively corresponding to the transducers 2a and generating sound ray data by adding the adjusted received signals (phase addition).

The image generation unit 14 generates B-mode image data by performing envelope detection, logarithmic amplification and the like on the sound ray data from the reception unit 13 and performing brightness conversion by performing gain adjustment and the like. In other words, B-mode image data is data where intensities of received signals are expressed in terms of brightness. The B-mode image data which is generated in the image generation unit 14 is transmitted to the image processing unit 15. Further, the image generation unit 14 includes the harmonic component extraction unit 14a.

The harmonic component extraction unit 14a performs pulse inversion and extracts harmonic components from the received signals which are output from the reception unit 13. In the embodiment, a second harmonic component can be extracted by the harmonic component extraction unit 14a. A second harmonic component can be extracted by filtering after adding (composition) the received signals obtained from the reflected ultrasounds corresponding to the two transmission ultrasounds respectively generated from the above mentioned first pulse signal and second pulse signal and removing the fundamental wave component included in the added received signal.

The image processing unit 15 includes an image memory unit 15a constituted of a semiconductor memory such as a DRAM (Dynamic Random Access Memory). The image processing unit 15 stores B-mode image data output from the image generation unit 14 in the image memory unit 15a in frame units. The image data in frame units may be called ultrasound image data or frame image data. The image processing unit 15 arbitrarily reads out the ultrasound image data stored in the image memory unit 15a and outputs the ultrasound image data to the DSC 16.

The DSC 16 converts the ultrasound image data received by the image processing unit 15 into an image signal of television signal scan mode and outputs the image signal to the display unit 17.

As for the display unit 17, display apparatuses such as a LCD (Liquid Crystal Display), a CRT (Cathode-Ray Tube) display, an organic EL (Electronic Luminescence) display, an inorganic EL display or a plasma display can be applied. The display unit 17 displays an ultrasound image on the display screen according to the image signal output from the DSC 16.

The control unit 18 includes a CPU (Central Processing Unit), a ROM (Read Only Memory) and a RAM (Random Access Memory), for example. The control unit 18 reads out and opens various types of programs such as a system program stored in the ROM in the RAM and collectively controls the operations of the components in the ultrasound diagnostic imaging apparatus S in compliance with the opened programs.

The ROM is configured of a non-volatile memory of semiconductor or the like, and stores a system program corresponding to the ultrasound diagnostic imaging apparatus S, various types of processing programs which can be executed on the system program, various types of data and the like. These programs are stored in the forms of program codes which can be read by a computer and the CPU sequentially executes the operations according to the program codes.

The RAM forms a work area in which various types of programs to be executed by the CPU and data relating to these programs are to be stored temporarily.

Embodiment 1

Hereinafter, the present invention will be described in detail in terms of embodiment examples. However, it is needless to say that the present invention is not limited to the embodiment examples in any way.

Embodiment Example 1

Figure 6:
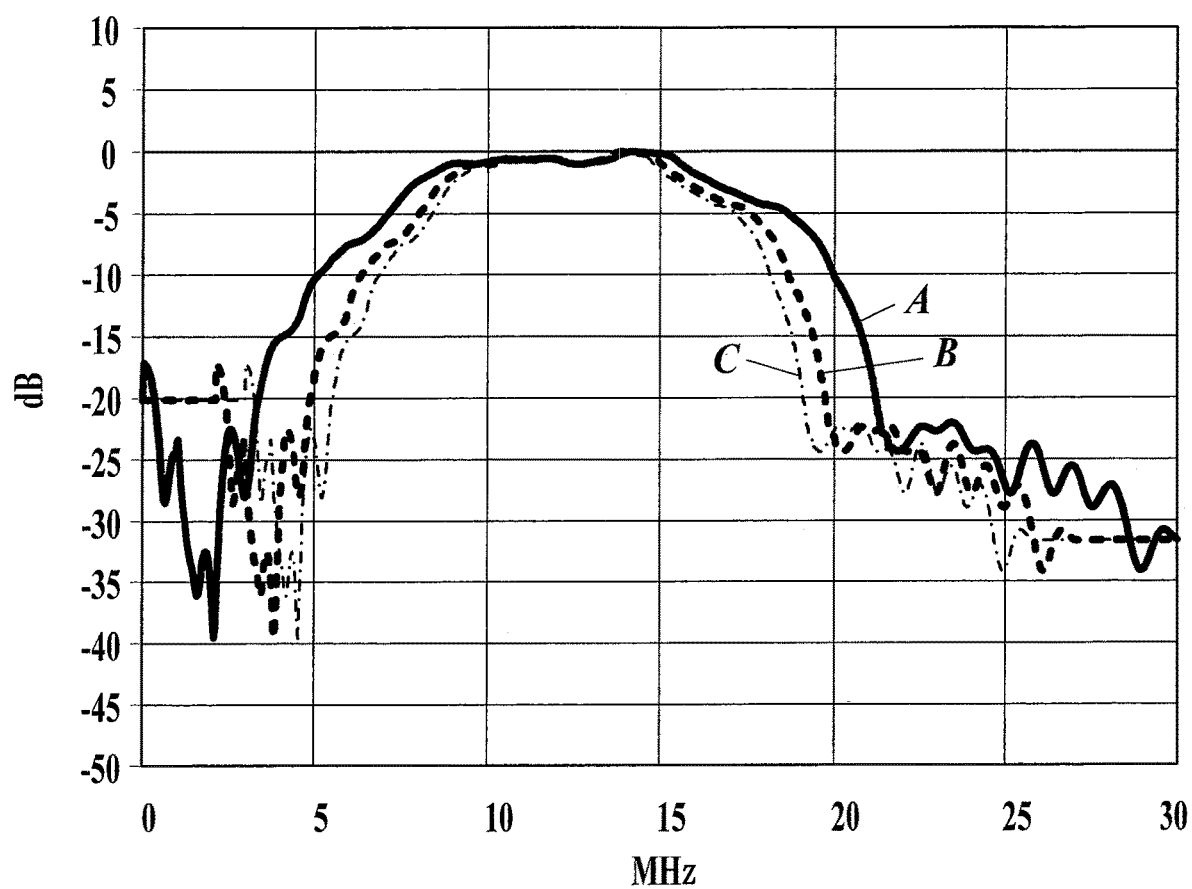
FIG. 6 is a drawing for explaining a transmission bandwidth of the ultrasound probe.

First, as for the above mentioned ultrasound probe 2, an ultrasound probe having the following characteristics is used, the characteristics being: the minimum frequency (FL20) at −20 dB in transmission is 3.4 MHz; the maximum frequency (FH20) at −20 dB in transmission is 21.2 MHz; the center frequency (FC20) is 12.3 MHz and the fractional bandwidth at −20 dB in transmission is 145%. This ultrasound probe is referred to as the ultrasound probe A. The line A in FIG. 6 shows the transmission bandwidth shape of the ultrasound probe A. In FIG. 6, the horizontal axis indicates frequency and the vertical axis indicates sensitivity.

Figure 7A:
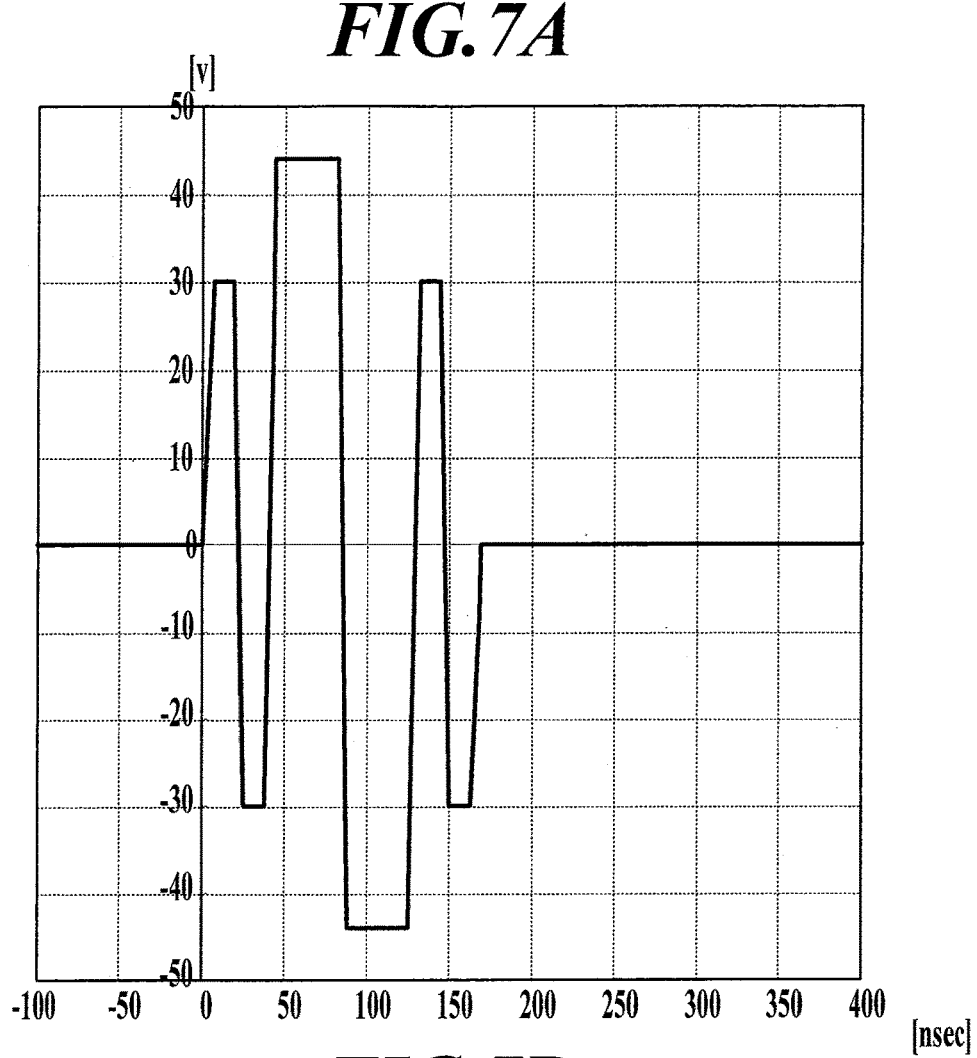
FIG. 7A is a drawing for explaining an example of a drive waveform of a pulse signal.
Figure 7B:
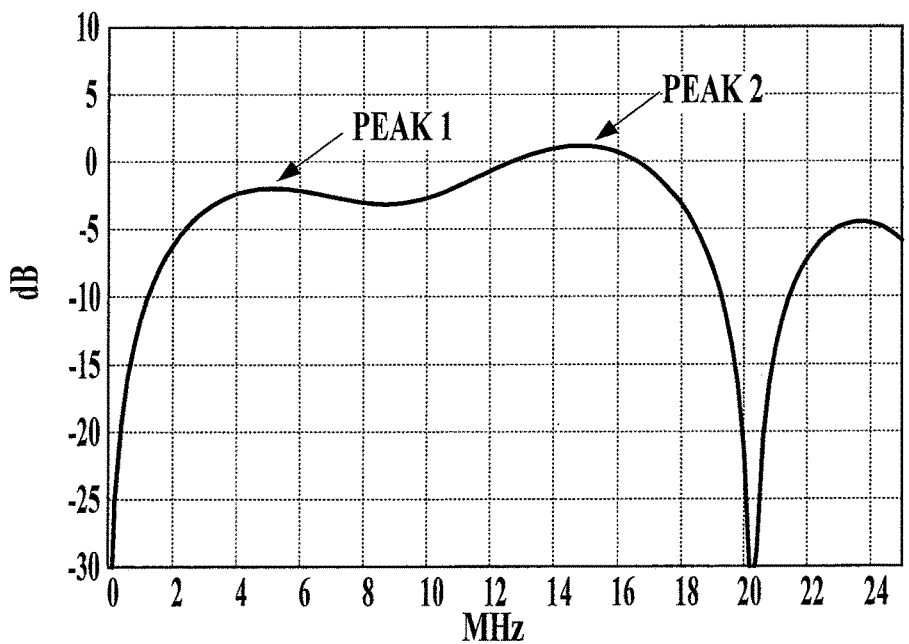
FIG. 7B is a drawing showing frequency power spectrum obtained by performing frequency analysis on the pulse signal shown in FIG. 7A.
Figure 15:
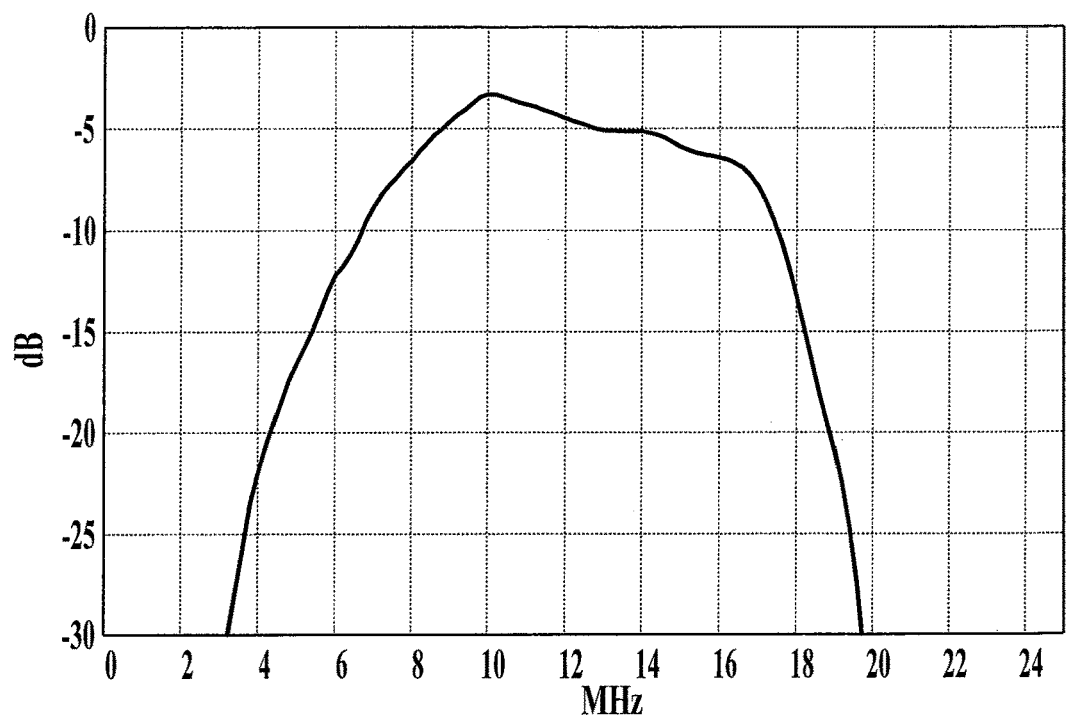
FIG. 15 is a drawing for explaining spectrum of transmission ultrasound.

A pulse signal output from the transmission unit 12 has a drive waveform as shown in FIG. 7A, and this is referred to as the drive waveform 1. The frequency power spectrum obtained by performing frequency analysis on this drive waveform is shown in FIG. 7B. In FIG. 7A, the horizontal axis indicates time and the vertical axis indicates voltage. In FIG. 7B, the horizontal axis indicates frequency and the vertical axis indicates signal intensity. When frequency analysis is performed on this drive waveform, the minimum frequency at −20 dB is 0.6 MHz, the maximum frequency at −20 dB is 20 MHz and the center frequency is 9.7 MHz. Further, this drive waveform gives two intensity peaks in the transmission frequency band (3.4 MHz-21.2 MHz) at −20 dB of the ultrasound probe A. At the first peak (peak 1), the frequency is 5.2 MHz and the intensity is −2.0 dB and at the second peak (peak 2), the frequency is 14.8 MHz and the intensity is 1.2 dB. Further, the frequency component at the frequency (12.3 MHz) same as the center frequency in the transmission frequency band of the ultrasound probe A has the intensity of −0.4 dB. The spectrum of the transmission ultrasound which is output due to the pulse signal of the drive waveform 1 being applied to the ultrasound probe A is shown in FIG. 15.

Embodiment Example 2

As for the ultrasound probe 2, the ultrasound probe A same as that in Embodiment example 1 is used.

Figure 8A:
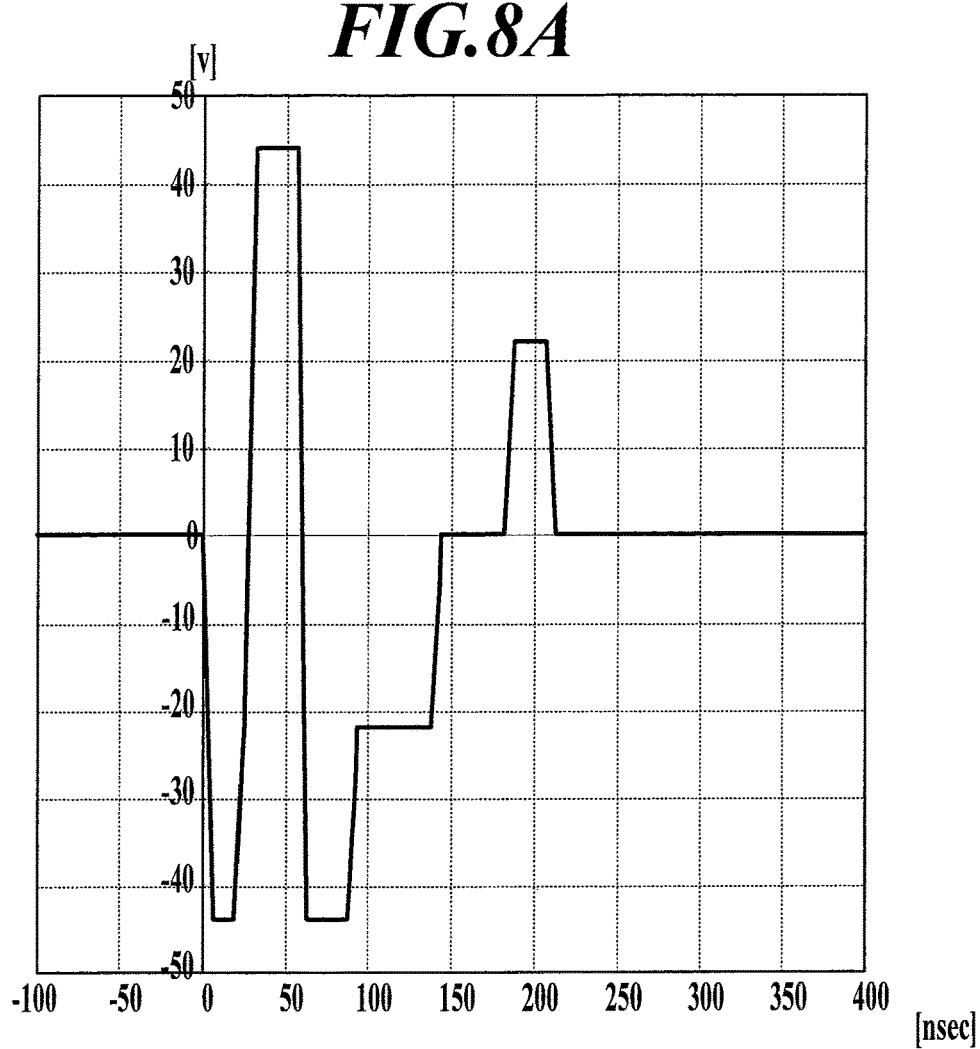
FIG. 8A is a drawing for explaining an example of a drive waveform of a pulse signal.
Figure 8B:
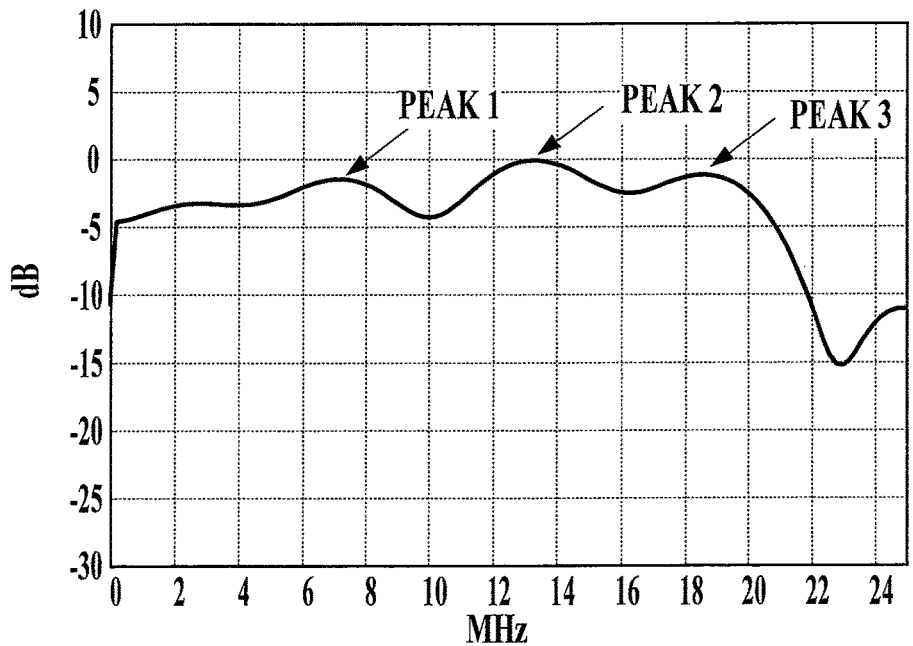
FIG. 8B is a drawing showing frequency power spectrum obtained by performing frequency analysis on the pulse signal shown in FIG. 8A.
Figure 16:
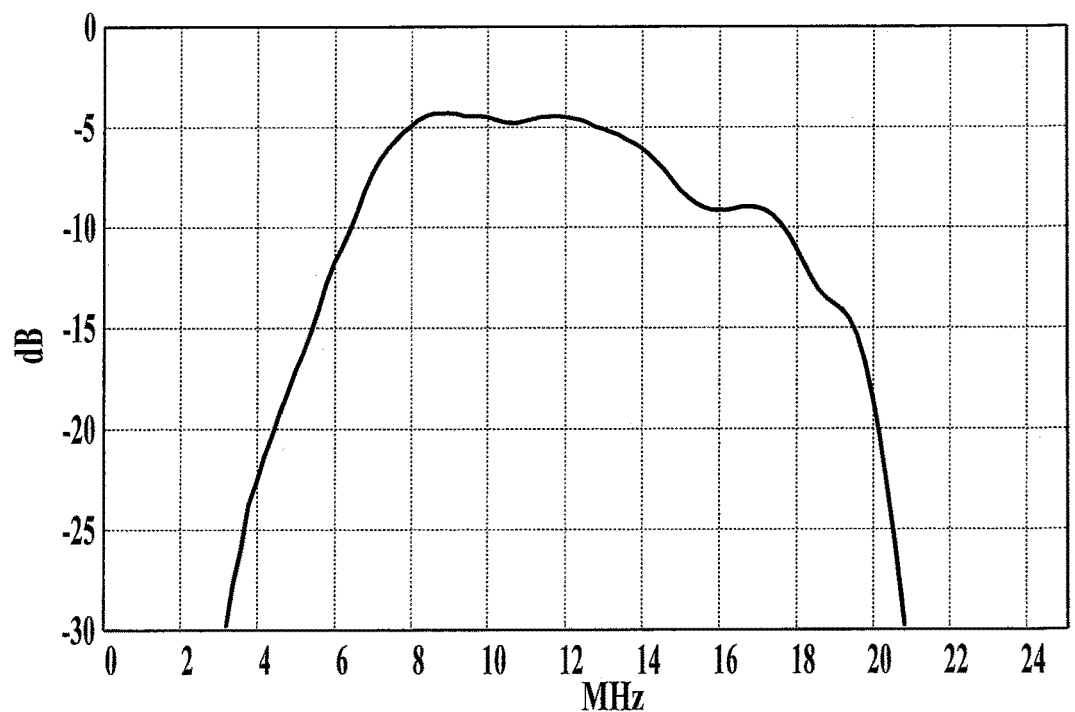
FIG. 16 is a drawing for explaining spectrum of transmission ultrasound.

A pulse signal output from the transmission unit 12 has a drive waveform as shown in FIG. 8A, and this is referred to as the drive waveform 2. The frequency power spectrum obtained by performing frequency analysis on this drive waveform is shown in FIG. 8B. In FIG. 8A, the horizontal axis indicates time and the vertical axis indicates voltage. In FIG. 8B, the horizontal axis indicates frequency and the vertical axis indicates signal intensity. When frequency analysis is performed on this drive waveform, the minimum frequency at −20 dB is 0.4 MHz, the maximum frequency at −20 dB is 27.2 MHz and the center frequency is 13.8 MHz. Further, this drive waveform gives three intensity peaks in the transmission frequency band (3.4 MHz-21.2 MHz) at −20 dB of the ultrasound probe A. At the first peak (peak 1), the frequency is 7.2 MHz and the intensity is −1.3 dB, at the second peak (peak 2), the frequency is 13.4 MHz and the intensity is 0.1 dB and at the third peak (peak 3), the frequency is 18.6 MHz and the intensity is −1.0. Further, the frequency component at the frequency (12.3 MHz) same as the center frequency in the transmission frequency band of the ultrasound probe A has the intensity of −0.5 dB. The spectrum of the transmission ultrasound which is output due to the pulse signal of the drive waveform 2 being applied to the ultrasound probe A is shown in FIG. 16.

Comparison Example 1

As for the ultrasound probe 2, the ultrasound probe A same as that in Embodiment example 1 is used.

Figure 9A:
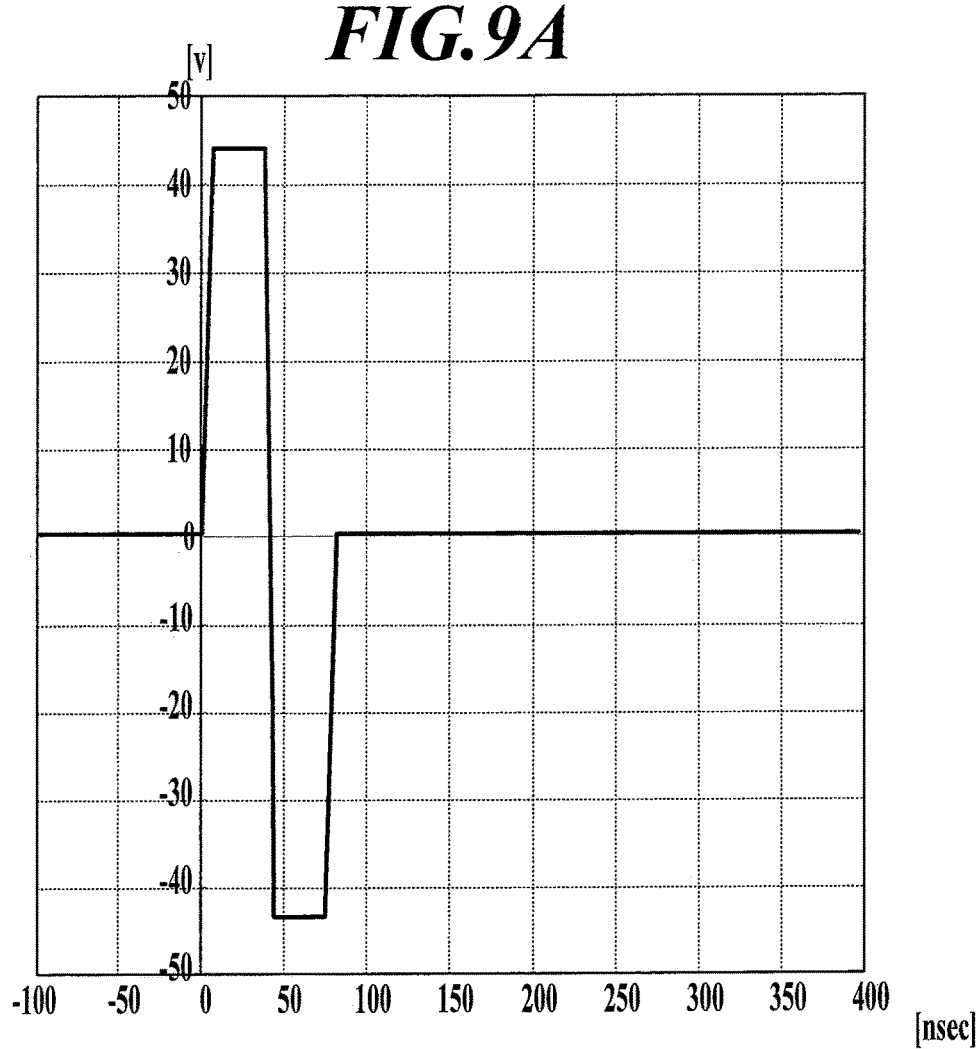
FIG. 9A is a drawing for explaining an example of a drive waveform of a pulse signal.
Figure 9B:
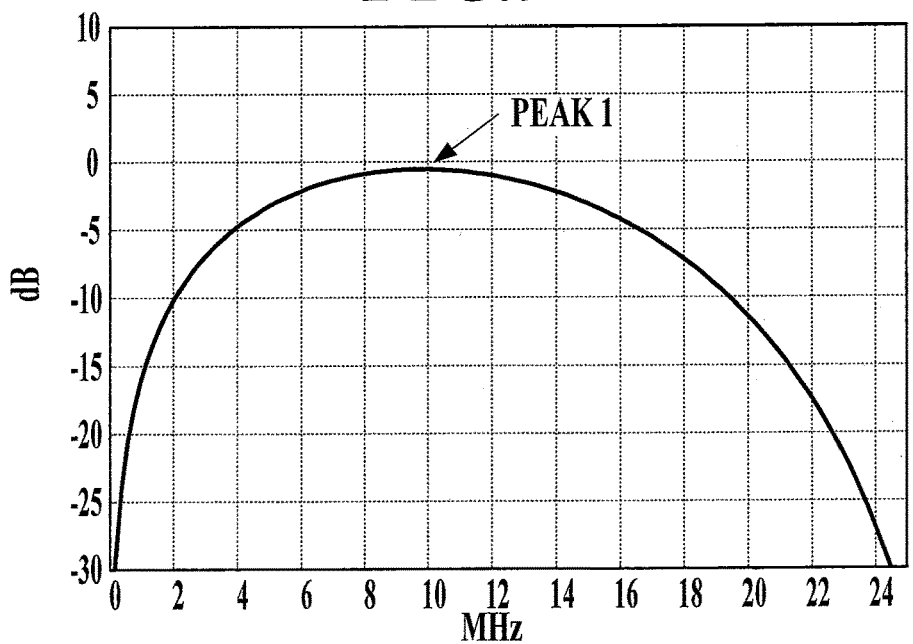
FIG. 9B is a drawing showing frequency power spectrum obtained by performing frequency analysis on the pulse signal shown in FIG. 9A.
Figure 17:
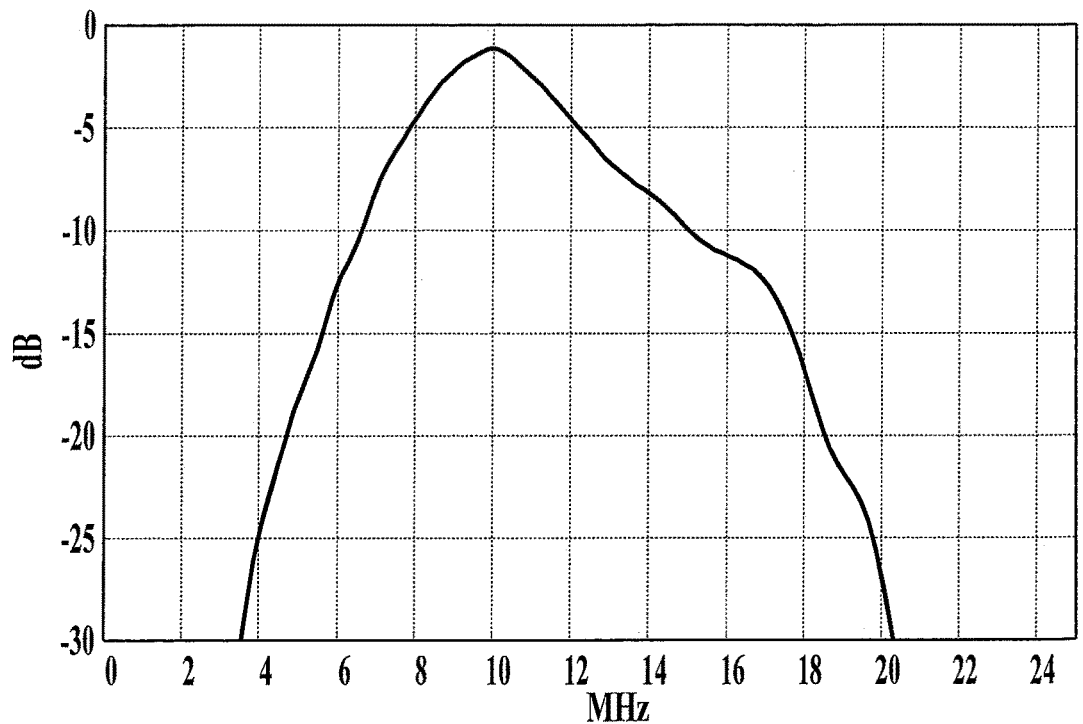
FIG. 17 is a drawing for explaining spectrum of transmission ultrasound.

A pulse signal output from the transmission unit 12 has a drive waveform as shown in FIG. 9A, and this is referred to as the drive waveform 3. The frequency power spectrum obtained by performing frequency analysis on this drive waveform is shown in FIG. 9B. In FIG. 9A, the horizontal axis indicates time and the vertical axis indicates voltage. In FIG. 9B, the horizontal axis indicates frequency and the vertical axis indicates signal intensity. When frequency analysis is performed on this drive waveform, the minimum frequency at −20 dB is 0.6 MHz, the maximum frequency at −20 dB is 22.8 MHz and the center frequency is 11.7 MHz. Further, this drive waveform gives one intensity peak in the transmission frequency band (3.4 MHz-21.2 MHz) at −20 dB of the ultrasound probe A. At the first peak (peak 1), the frequency is 9.8 MHz and the intensity is −0.4 dB. Further, the frequency component at the frequency (12.3 MHz) same as the center frequency in the transmission frequency band of the ultrasound probe A has the intensity of −1.0 dB. The spectrum of the transmission ultrasound which is output due to the pulse signal of the drive waveform 3 being applied to the ultrasound probe A is shown in FIG. 17.

Comparison Example 2

As for the ultrasound probe 2, the ultrasound probe A same as that in Embodiment example 1 is used.

Figure 10A:
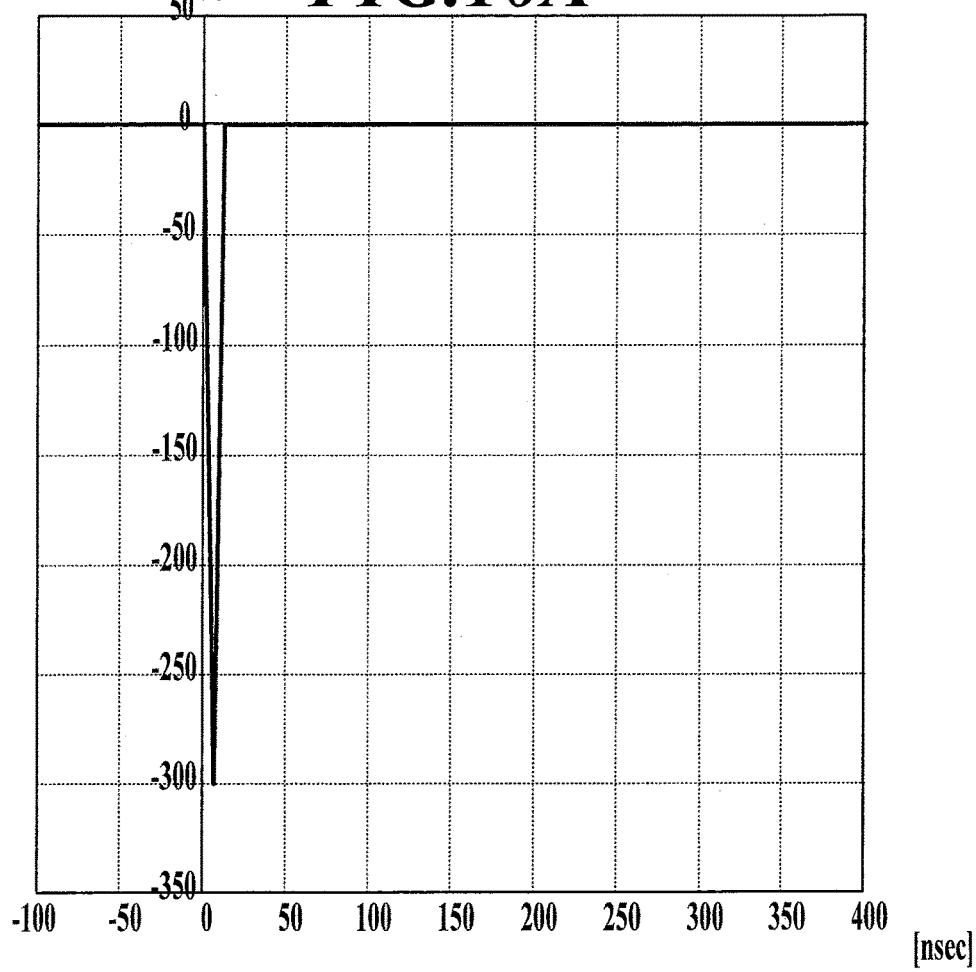
FIG. 10A is a drawing for explaining an example of a drive waveform of a pulse signal.
Figure 10B:
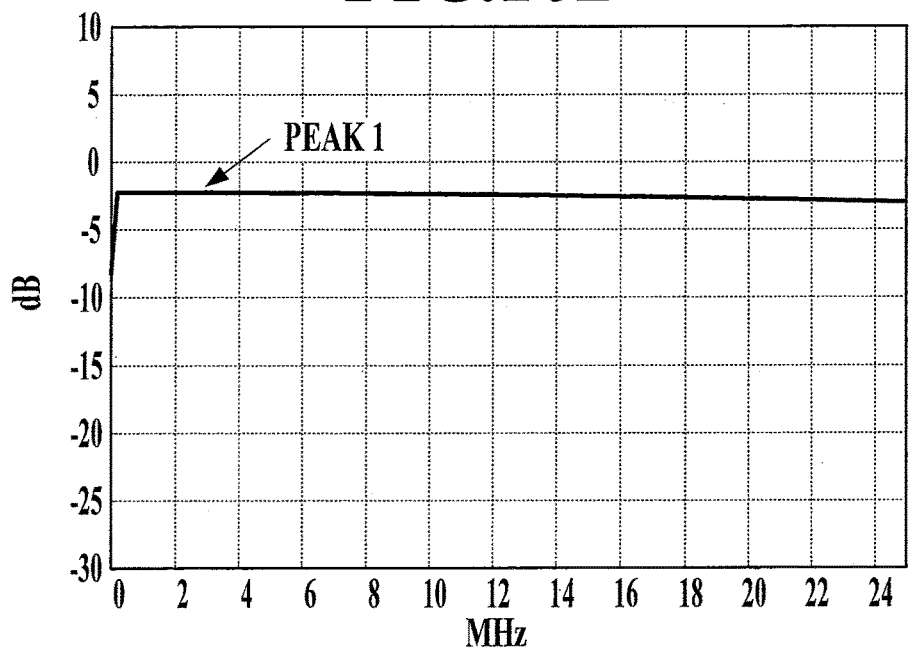
FIG. 10B is a drawing showing frequency power spectrum obtained by performing frequency analysis on the pulses signal shown in FIG. 10A.
Figure 18:
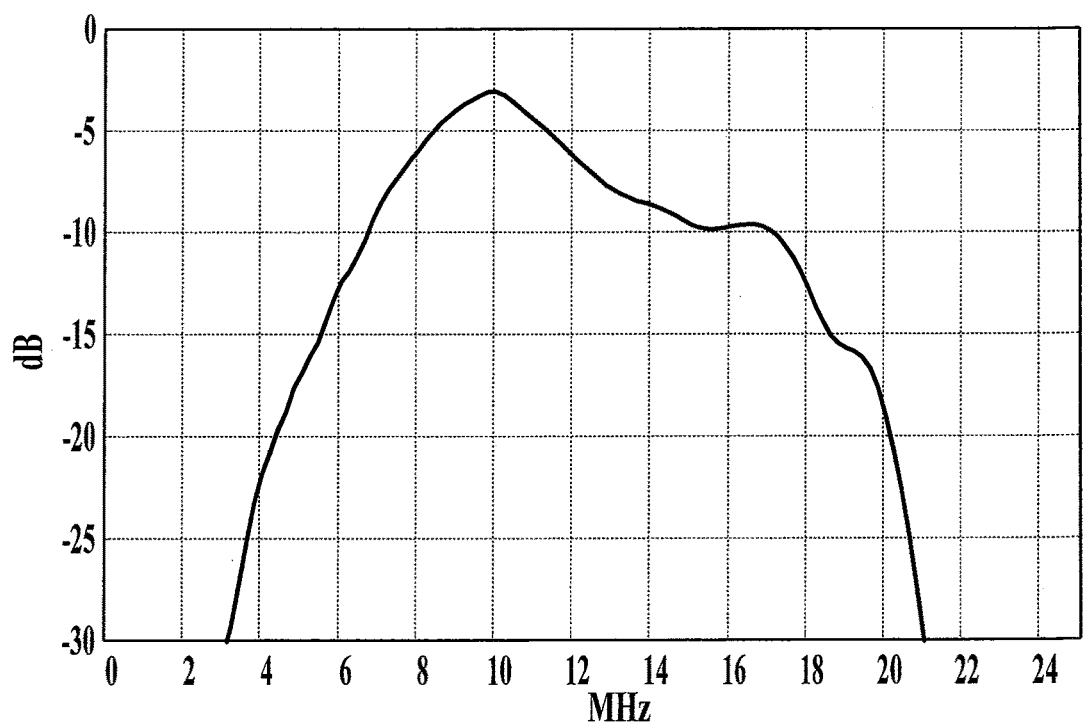
FIG. 18 is a drawing for explaining spectrum of transmission ultrasound.

A pulse signal output from the transmission unit 12 has a drive waveform as shown in FIG. 10A, and this is referred to as the drive waveform 4. The frequency power spectrum obtained by performing frequency analysis on this drive waveform is shown in FIG. 10B. In FIG. 10A, the horizontal axis indicates time and the vertical axis indicates voltage. In FIG. 10B, the horizontal axis indicates frequency and the vertical axis indicates signal intensity. When frequency analysis is performed on this drive waveform, the minimum frequency at −20 dB is 0.2 MHz, the maximum frequency at −20 dB is 114 MHz and the center frequency is 57 MHz. Further, this drive waveform gives one intensity peak in the transmission frequency band (3.4 MHz-21.2 MHz) at −20 dB of the ultrasound probe A. At the first peak (peak 1), the frequency is 3.4 MHz and the intensity is −2.2 dB. Further, the frequency component at the frequency (12.3 MHz) same as the center frequency in the transmission frequency band of the ultrasound probe A has the intensity of −2.3 dB. The spectrum of the transmission ultrasound which is output due to the pulse signal of the drive waveform 4 being applied to the ultrasound probe A is shown in FIG. 18.

Embodiment Example 3

As for the ultrasound probe 2, the ultrasound probe A same as that in Embodiment example 1 is used. Further, the drive waveform of the pulse signal output from the transmission unit 12 is the same as the drive waveform 1 in Embodiment example 1.

Embodiment Example 4

As for the ultrasound probe 2, the ultrasound probe A same as that in Embodiment example 1 is used. Further, the drive waveform of the pulse signal output from the transmission unit 12 is the same as the drive waveform 2 in Embodiment example 2.

Embodiment Example 5

As for the ultrasound probe 2, the ultrasound probe A same as that in Embodiment example 1 is used.

Figure 11A:
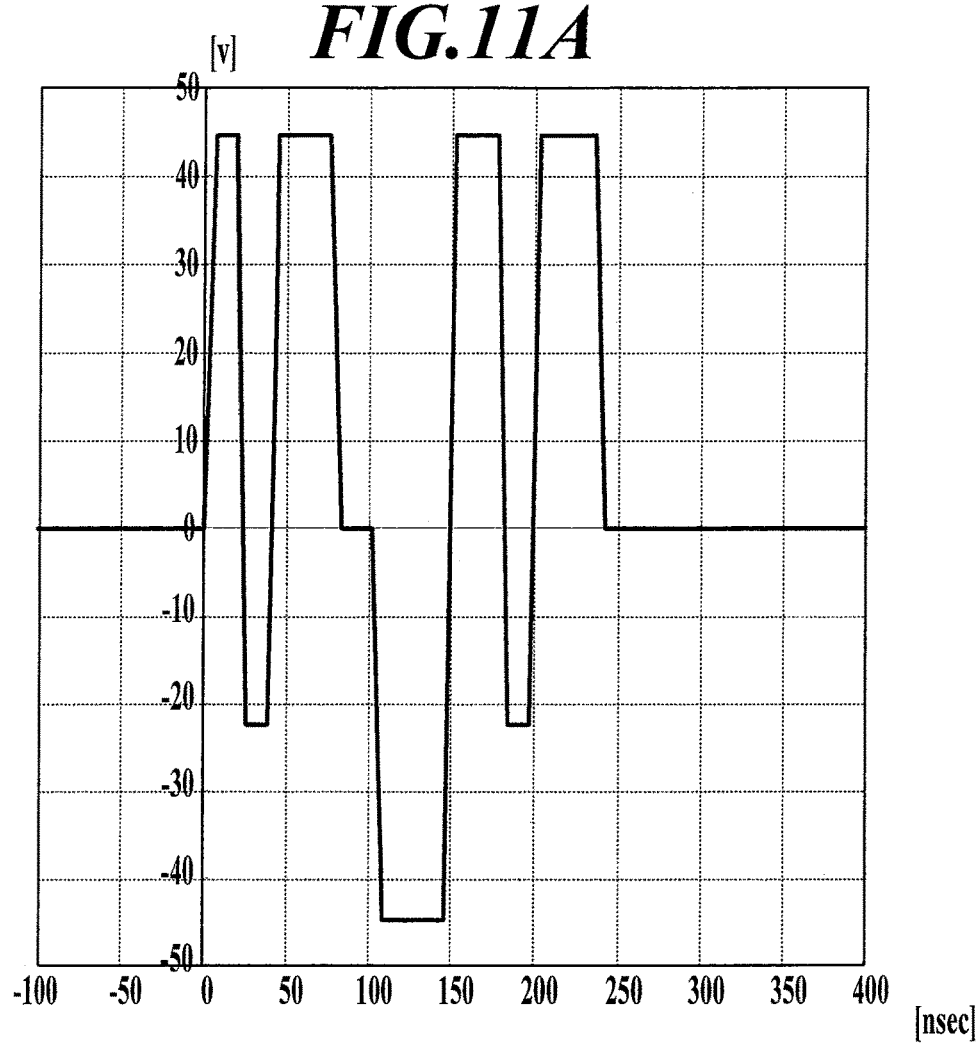
FIG. 11A is a drawing for explaining an example of a drive waveform of a pulse signal.
Figure 11B:
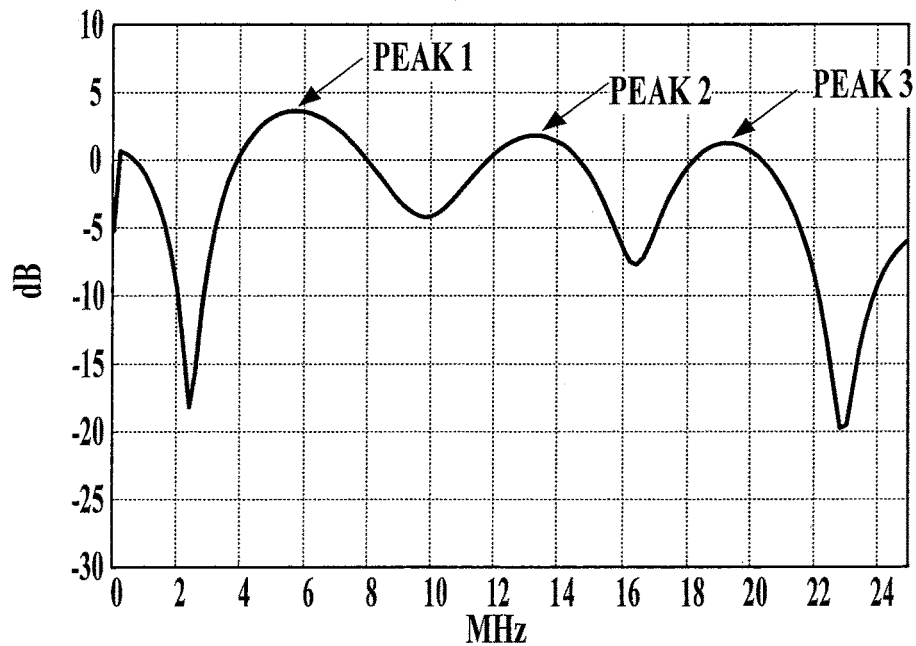
FIG. 11B is a drawing showing frequency power spectrum obtained by performing frequency analysis on the pulse signal shown in FIG. 11A.
Figure 19:
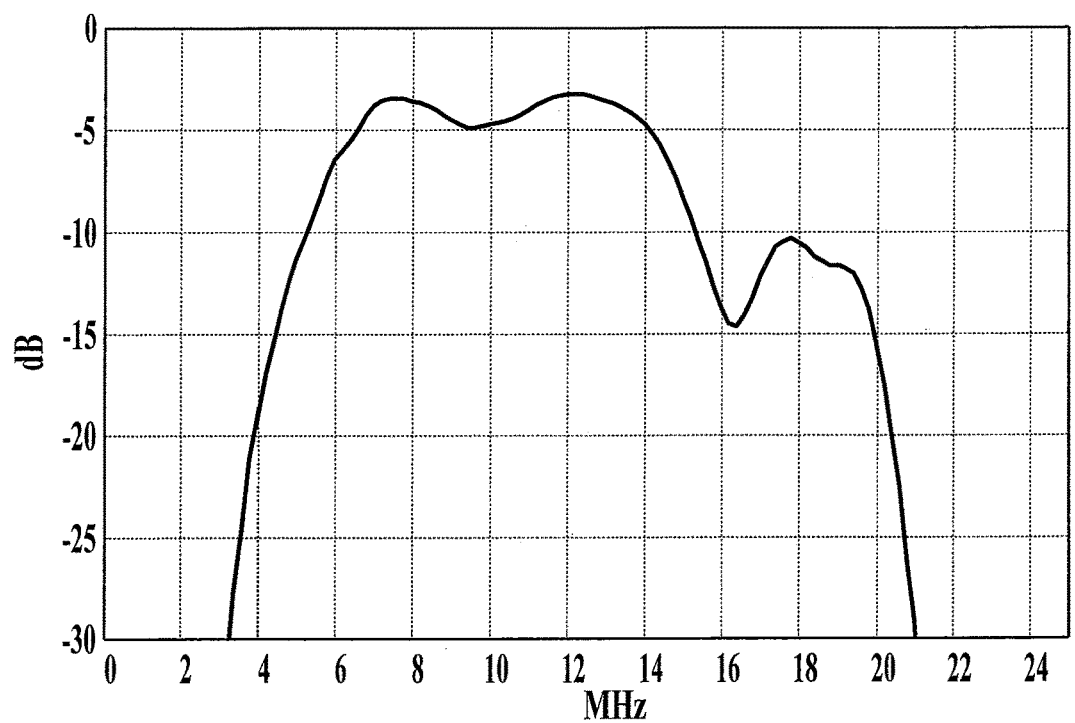
FIG. 19 is a drawing for explaining spectrum of transmission ultrasound.

A pulse signal output from the transmission unit 12 has a drive waveform as shown in FIG. 11A, and this is referred to as the drive waveform 5. The frequency power spectrum obtained by performing frequency analysis on this drive waveform is shown in FIG. 11B. In FIG. 11A, the horizontal axis indicates time and the vertical axis indicates voltage. In FIG. 11B, the horizontal axis indicates frequency and the vertical axis indicates signal intensity. When frequency analysis is performed on this drive waveform, the minimum frequency at −20 dB is 2.6 MHz, the maximum frequency at −20 dB is 22.8 MHz and the center frequency is 12.7 MHz. Further, this drive waveform gives three intensity peaks in the transmission frequency band (3.4 MHz-21.2 MHz) at −20 dB of the ultrasound probe A. At the first peak (peak 1), the frequency is 5.8 MHz and the intensity is 3.8 dB, at the second peak (peak 2), the frequency is 13.2 MHz and the intensity is 2.0 dB and at the third peak (peak 3), the frequency is 19.2 MHz and the intensity is 1.4. Further, the frequency component at the frequency (12.3 MHz) same as the center frequency in the transmission frequency band of the ultrasound probe A has the intensity of 1.1 dB. The spectrum of the transmission ultrasound which is output due to the pulse signal of the drive waveform 5 being applied to the ultrasound probe A is shown in FIG. 19.

Embodiment Example 6

As for the above mentioned ultrasound probe 2, an ultrasound probe having the following characteristics is used, the characteristics being: the minimum frequency (FL20) at −20 dB in transmission is 4.9 MHz; the maximum frequency (FH20) at −20 dB in transmission is 19.7 MHz; the center frequency (FC20) is 12.3 MHz and the fractional bandwidth at −20 dB in transmission is 120%. This ultrasound probe is referred to as the ultrasound probe B. The line Bin FIG. 6 shows the transmission bandwidth shape of the ultrasound probe B.

The drive waveform of the pulse signal output from the transmission unit 12 is same as the drive waveform 5 in Embodiment example 5. This drive waveform gives three intensity peaks in the transmission frequency band (4.9 MHz-19.7 MHz) at −20 dB of the ultrasound probe B. At the first peak (peak 1), the frequency is 5.8 MHz and the intensity is 3.8 dB, at the second peak (peak 2), the frequency is 13.2 MHz and the intensity is 2.0 dB and at the third peak (peak 3), the frequency is 19.2 MHz and the intensity is 1.4. Further, the frequency component at the frequency (12.3 MHz) same as the center frequency in the transmission frequency band of the ultrasound probe B has the intensity of 1.1 dB.

Embodiment Example 7

As for the ultrasound probe 2, an ultrasound probe having the following characteristics is used, the characteristics being: the minimum frequency (FL20) at −20 dB in transmission is 5.6 MHz; the maximum frequency (FH20) at −20 dB in transmission is 19.1 MHz; the center frequency (FC20) is 12.3 MHz and the fractional bandwidth at −20 dB in transmission is 109%. This ultrasound probe is referred to as the ultrasound probe C. The line C in FIG. 6 shows the transmission bandwidth shape of the ultrasound probe C.

The drive waveform of the pulse signal output from the transmission unit 12 is same as the drive waveform 5 in Embodiment example 5. This drive waveform gives three intensity peaks in the transmission frequency band (5.6 MHz-19.1 MHz) at −20 dB of the ultrasound probe C. At the first peak (peak 1), the frequency is 5.8 MHz and the intensity is 3.8 dB, at the second peak (peak 2), the frequency is 13.2 MHz and the intensity is 2.0 dB and at the third peak (peak 3), the frequency is 19.2 MHz and the intensity is 1.4. Further, the frequency component at the frequency (12.3 MHz) same as the center frequency in the transmission frequency band of the ultrasound probe C has the intensity of 1.1 dB.

Embodiment Example 8

As for the ultrasound probe 2, the ultrasound probe A same as that in Embodiment example 1 is used.

Figure 12A:
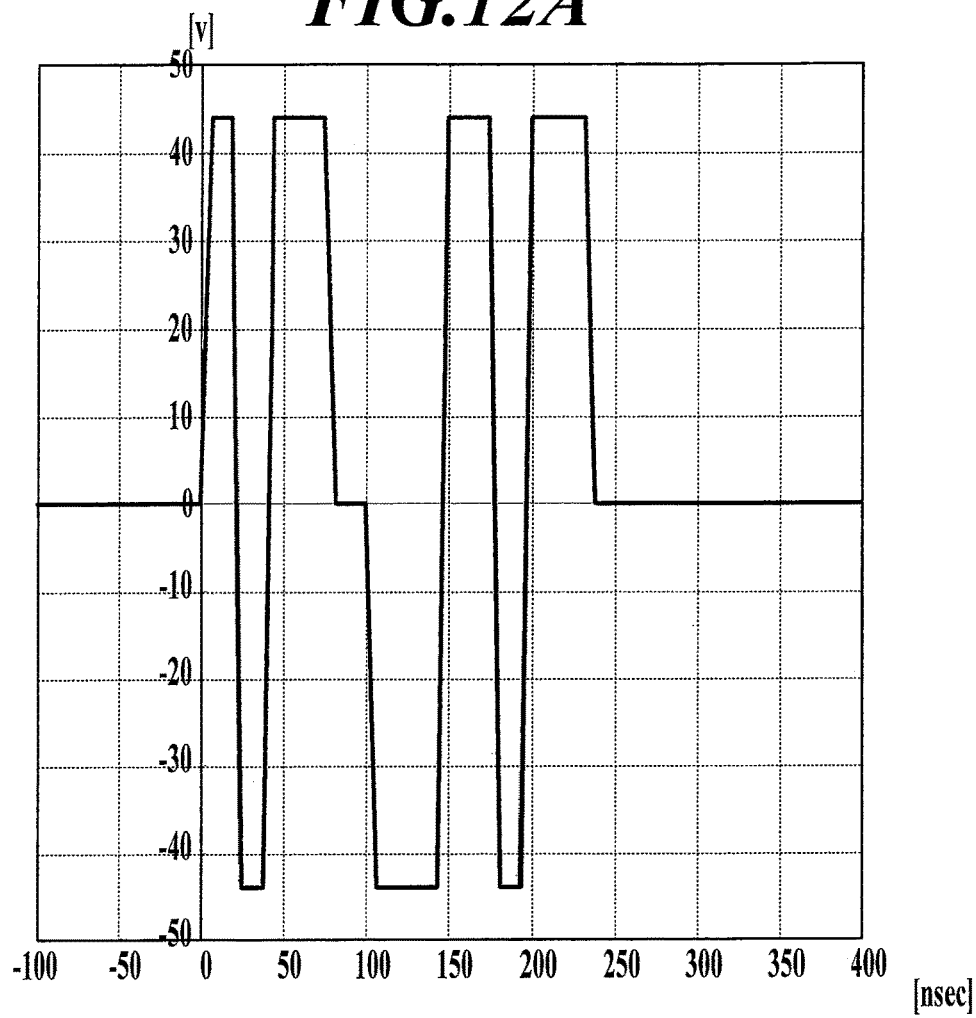
FIG. 12A is a drawing for explaining an example of a drive waveform of a pulse signal.
Figure 12B:
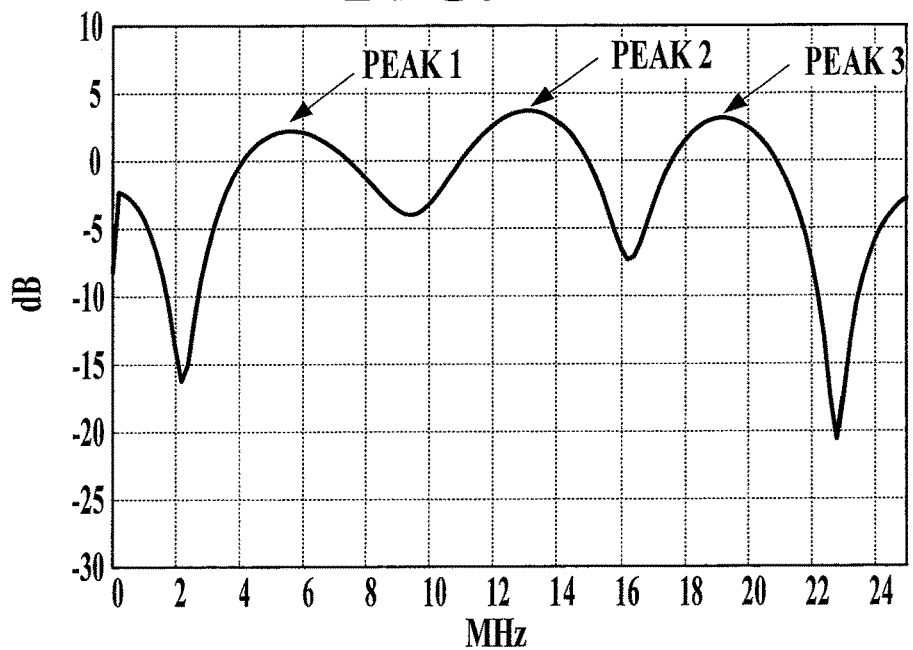
FIG. 12B is a drawing showing frequency power spectrum obtained by performing frequency analysis on the pulse signal shown in FIG. 12A.
Figure 20:
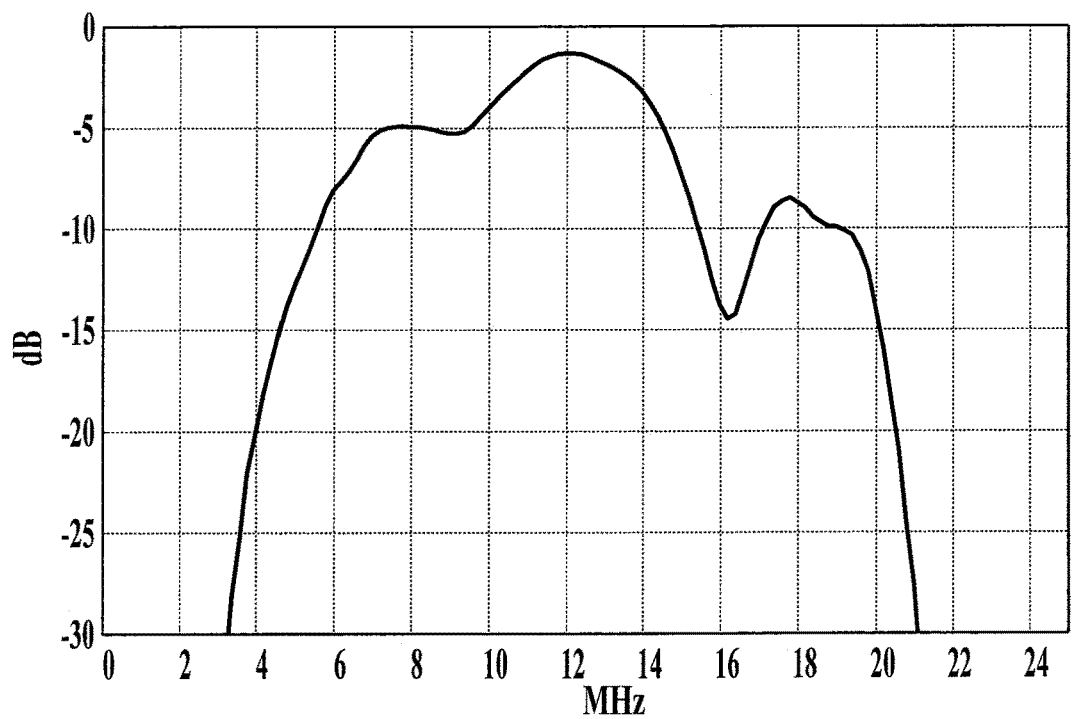
FIG. 20 is a drawing for explaining spectrum of transmission ultrasound.

A pulse signal output from the transmission unit 12 has a drive waveform as shown in FIG. 12A, and this is referred to as the drive waveform 6. The frequency power spectrum obtained by performing frequency analysis on this drive waveform is shown in FIG. 12B. In FIG. 12A, the horizontal axis indicates time and the vertical axis indicates voltage. In FIG. 12B, the horizontal axis indicates frequency and the vertical axis indicates signal intensity. When frequency analysis is performed on this drive waveform, the minimum frequency at −20 dB is 2.2 MHz, the maximum frequency at −20 dB is 22.6 MHz and the center frequency is 12.4 MHz. Further, this drive waveform gives three intensity peaks in the transmission frequency band (3.4 MHz-21.2 MHz) at −20 dB of the ultrasound probe A. At the first peak (peak 1), the frequency is 5.6 MHz and the intensity is 2.2 dB, at the second peak (peak 2), the frequency is 13.2 MHz and the intensity is 3.7 dB and at the third peak (peak 3), the frequency is 19.2 MHz and the intensity is 3.1. Further, the frequency component at the frequency (12.3 MHz) same as the center frequency in the transmission frequency band of the ultrasound probe A has the intensity of 3.1 dB. The spectrum of the transmission ultrasound which is output due to the pulse signal of the drive waveform 6 being applied to the ultrasound probe A is shown in FIG. 20.

Embodiment Example 9

As for the ultrasound probe 2, the ultrasound probe A same as that in Embodiment example 1 is used.

Figure 13A:
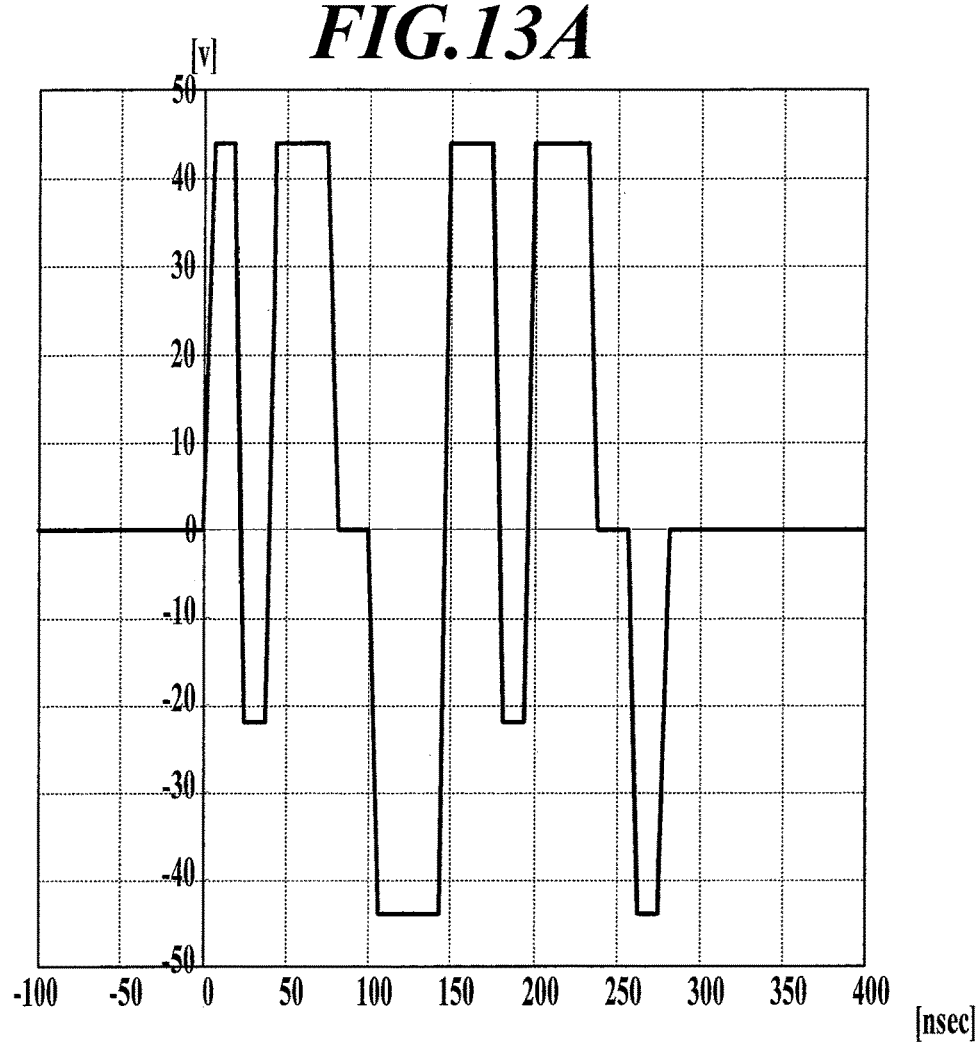
FIG. 13A is a drawing for explaining an example of a drive waveform of a pulse signal.
Figure 13B:
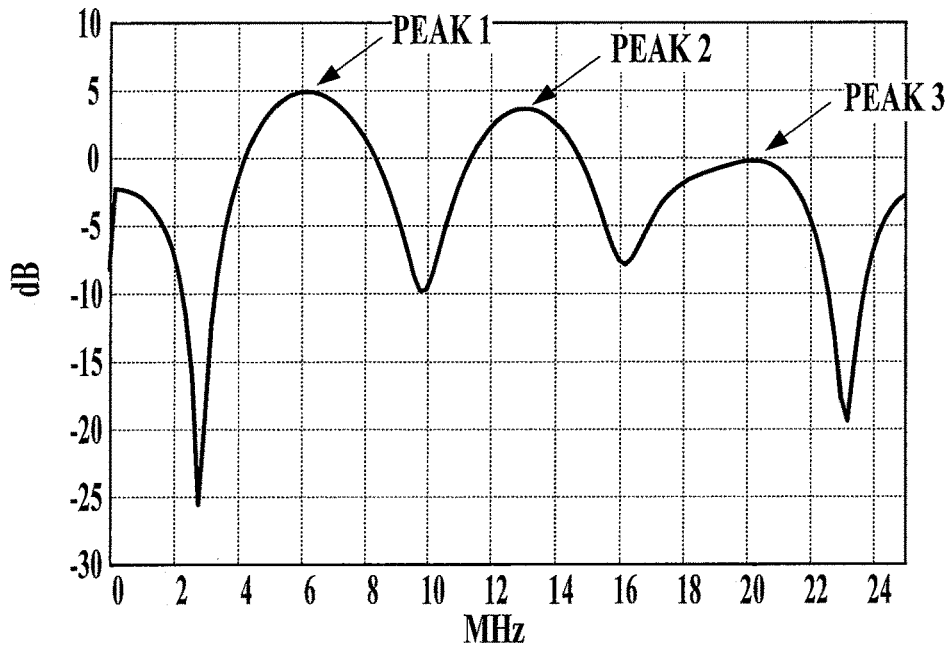
FIG. 13B is a drawing showing frequency power spectrum obtained by performing frequency analysis on the pulse signal shown in FIG. 13A.
Figure 21:
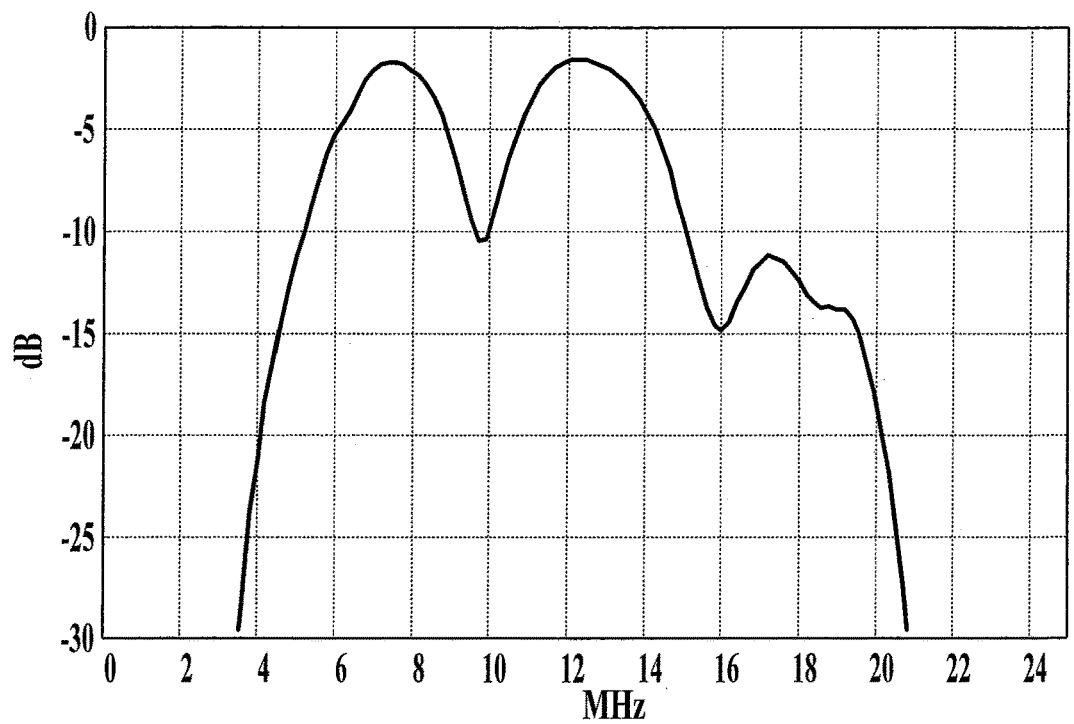
FIG. 21 is a drawing for explaining spectrum of transmission ultrasound.

A pulse signal output from the transmission unit 12 has a drive waveform as shown in FIG. 13A, and this is referred to as the drive waveform 7. The frequency power spectrum obtained by performing frequency analysis on this drive waveform is shown in FIG. 13B. In FIG. 13A, the horizontal axis indicates time and the vertical axis indicates voltage. In FIG. 13B, the horizontal axis indicates frequency and the vertical axis indicates signal intensity. When frequency analysis is performed on this drive waveform, the minimum frequency at −20 dB is 3.2 MHz, the maximum frequency at −20 dB is 23.0 MHz and the center frequency is 13.1 MHz. Further, this drive waveform gives three intensity peaks in the transmission frequency band (3.4 MHz-21.2 MHz) at −20 dB of the ultrasound probe A. At the first peak (peak 1), the frequency is 6.2 MHz and the intensity is 5.0 dB, at the second peak (peak 2), the frequency is 13.2 MHz and the intensity is 3.7 dB and at the third peak (peak 3), the frequency is 20.2 MHz and the intensity is −0.1. Further, the frequency component at the frequency (12.3 MHz) same as the center frequency in the transmission frequency band of the ultrasound probe A has the intensity of 2.9 dB. The spectrum of the transmission ultrasound which is output due to the pulse signal of the drive waveform 7 being applied to the ultrasound probe A is shown in FIG. 21.

Comparison Example 3

As for the ultrasound probe 2, the ultrasound probe A same as that in Embodiment example 1 is used.

Figure 14A:
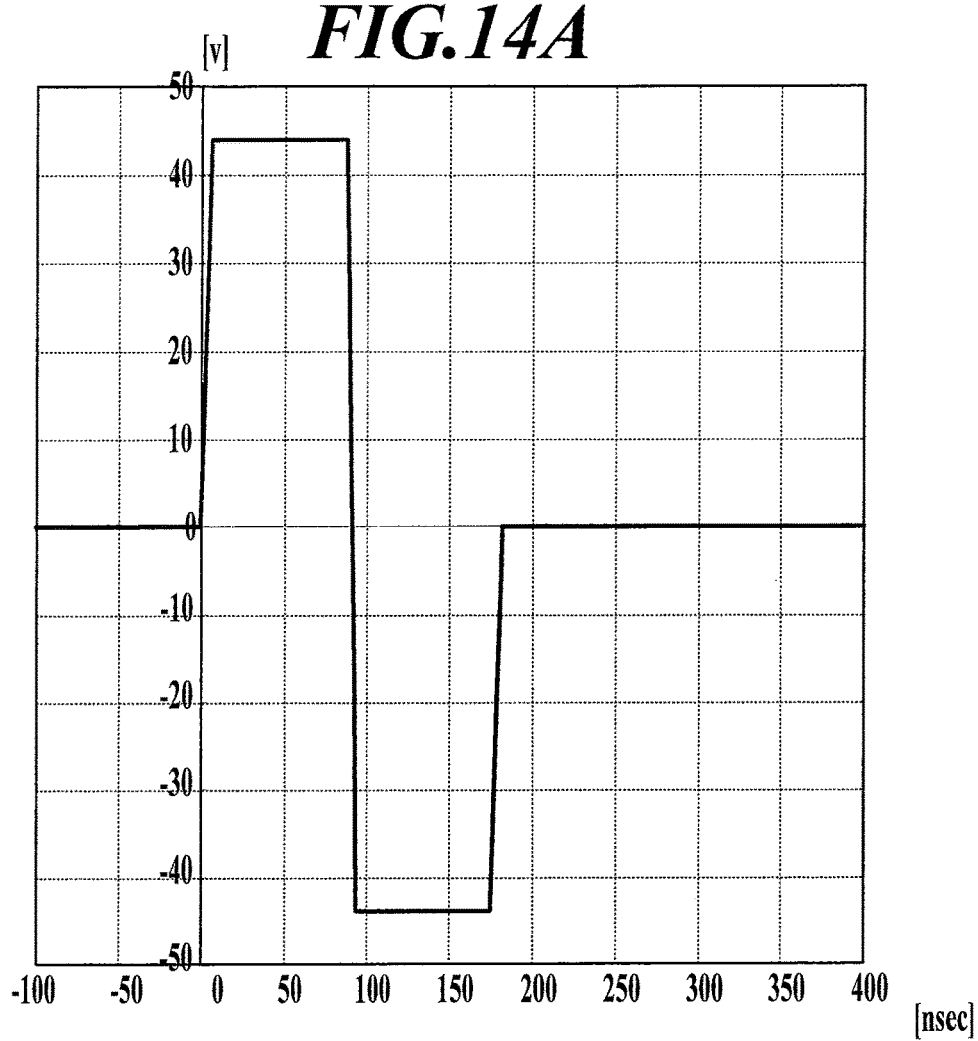
FIG. 14A is a drawing for explaining an example of a drive waveform of a pulse signal.
Figure 14B:
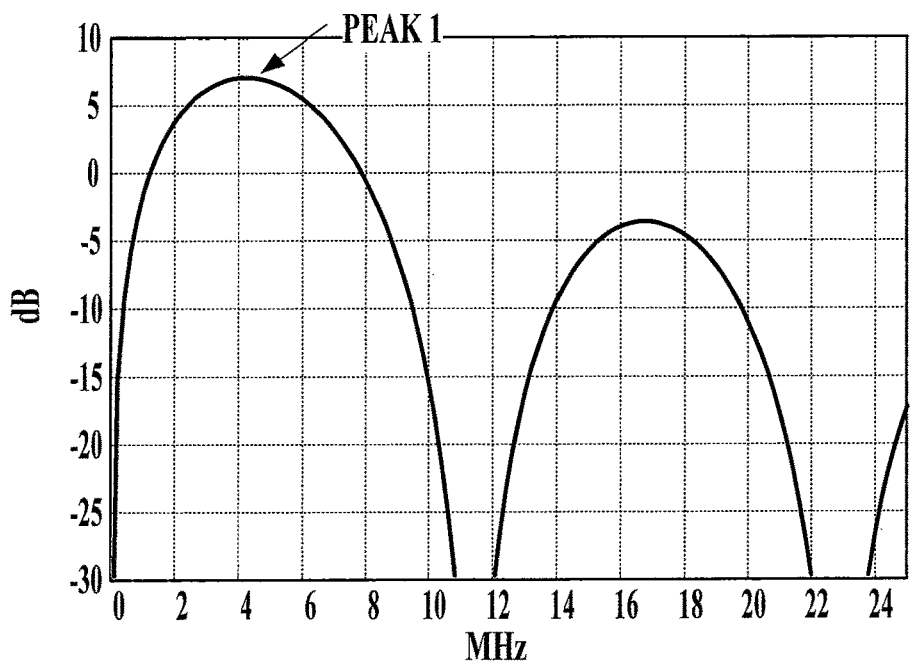
FIG. 14B is a drawing showing frequency power spectrum obtained by performing frequency analysis on the pulse signal shown in FIG. 14A.
Figure 22:
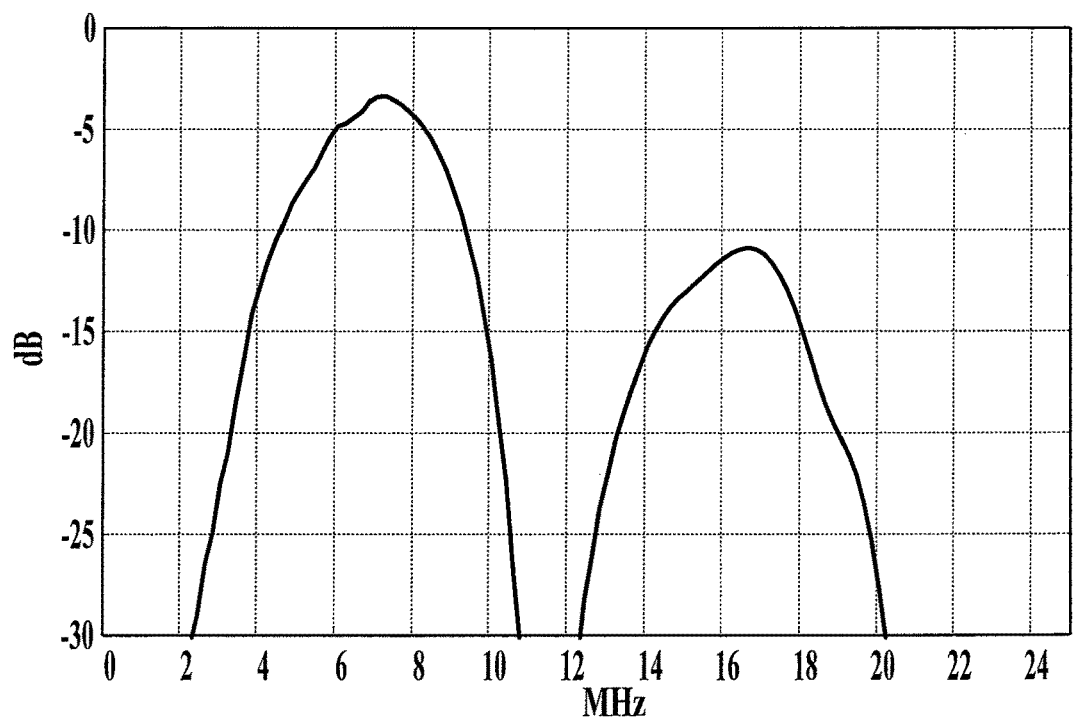
FIG. 22 is a drawing for explaining spectrum of transmission ultrasound.

A pulse signal output from the transmission unit 12 is a drive waveform as shown in FIG. 14A, and this is referred to as the drive waveform 8. The frequency power spectrum obtained by performing frequency analysis on this drive waveform is shown in FIG. 14B. In FIG. 14A, the horizontal axis indicates time and the vertical axis indicates voltage. In FIG. 14B, the horizontal axis indicates frequency and the vertical axis indicates signal intensity. When frequency analysis is performed on this drive waveform, the minimum frequency at −20 dB is 0.4 MHz, the maximum frequency at −20 dB is 9.8 MHz and the center frequency is 5.1 MHz. Further, this drive waveform gives one intensity peak in the transmission frequency band (3.4 MHz-21.2 MHz) at −20 dB of the ultrasound probe A. At the first peak (peak 1), the frequency is 4.2 MHz and the intensity is 7.0 dB. Further, the frequency component at the frequency (12.3 MHz) same as the center frequency in the transmission frequency band of the ultrasound probe A has the intensity of −25.6 dB. The spectrum of the transmission ultrasound which is output due to the pulse signal of the drive waveform 8 being applied to the ultrasound probe A is shown in FIG. 22.

Comparison Example 4

As for the ultrasound probe 2, the ultrasound probe A same as that in Embodiment example 1 is used. Further, the drive waveform of the pulse signal output from the transmission unit 12 is the same as the drive waveform 4 in Comparison example 2.

<Evaluation Method>

In an acoustic equivalent member same as RMI 404GS-LE0.5 manufactured by Gammex, 50 μm SUS wire is embedded at the 15 mm depth position. With respect to each of Embodiment example 1, Embodiment example 2, Comparison example 1 and Comparison example 2, a pulse signal of a drive waveform having the conditions shown in Table 1 is applied to the ultrasound probe and transmission and reception of ultrasound is performed, and an ultrasound image based on fundamental waves is obtained on the basis of the received signals obtained from the received ultrasound. On the other hand, with respect to each of Embodiment example 3 to Embodiment example 9, Comparison example 3 and Comparison example 4, the first pulse signal of a drive waveform having the conditions shown in Table 1 and the second pulse signal whose polarity is the inverse of that of the first pulse signal are applied to the same scanning line of the ultrasound probe with time interval therebetween and transmission and reception of the first ultrasound and the second ultrasound is performed. Then, the received signals obtained from the received first ultrasound and the received second ultrasound are combined by pulse inversion and an ultrasound image of THI (Tissue Harmonic Imaging) is obtained. At this time, the transmission focal point is at 15 mm. Further, the wire visualization brightness at the time of imaging is converted into acoustic intensity (dB) and 20 dB resolution (distance resolution, azimuth resolution) is obtained. Further, two frames of ultrasound images are obtained as described above, correlation between these two frames of ultrasound images is obtained, depth where this correlation is smaller than 0.5 is specified and this is set as the depth. Under their conditions in individual Embodiment examples 1 to 9 and Comparison examples 1 to 4, a wrist, a metacarpo phalangeal joint flexor tendon, a long head of biceps brachii tendon and a medial meniscu are vidualized. Then, they were evaluated based on the following evaluation criterion by the total of ten medical doctors and medical technologists who work in the fields related to orthopedics, and the values are averaged to obtain creation scores.

[Evaluation Criterion]

10: at the level excellent for recognizing the tissue condition

8: at the level practically sufficient for recognizing the tissue condition

6: not good but at the level where the tissue condition is recognizable

4: at the level where recognition of the tissue condition may be a problem

2: at the level where recognition of the tissue condition is difficult

These evaluation criterion are shown in the following table 1.

TABLE 1

| | | ultrasound probe | | | | drive waveform | | |
|---|---|---|---|---|---|---|---|---|
| | display mode | No. | center of bandwidth at −20 dB in transmission (MHz) | bandwidth at −20 dB in transmission (MHz-MHz) | fractional bandwidth at −20 dB in transmission | No. | center of bandwidth at −20 dB (MHz) | banckwidth at −20 dB (MHz-MHz) |
| Embodiment example 1 | fundamental wave | A | 12.3 | 3.4-21.2 | 145% | 1 | 9.7 | 0.6-20 |
| Embodiment example 2 | | | | | | 2 | 13.8 | 0.4-27.2 |
| Comparison example 1 | | | | | | 3 | 11.7 | 0.6-22.8 |
| Comparison example 2 | | | | | | 4 | 57 | 0.2-114 |
| Embodiment example 3 | THI | A | 12.3 | 3.4-21.2 | 145% | 1 | 9.7 | 0.6-20 |
| Embodiment example 4 | | | | | | 2 | 13.8 | 0.4-27.2 |
| Embodiment example 5 | | | | | | 5 | 12.7 | 2.6-22.8 |
| Embodiment example 6 | | B | 12.3 | 4.9-19.7 | 120% | | | |
| Embodiment example 7 | | C | 12.3 | 5.6-19.1 | 109% | | | |
| Embodiment example 8 | | A | 12.3 | 3.4-21.2 | 145% | 6 | 12.4 | 2.2-22.6 |
| Embodiment example 9 | | | | | | 7 | 13.1 | 3.2-23.0 |
| Comparison example 3 | | | | | | 8 | 5.1 | 0.4-9.8 |
| Comparison example 4 | | | | | | 4 | 57 | 0.2-114 |

| | drive waveform | | | | | | center of bandwidth at −20 dB in probe transmission (MHz) | |
|---|---|---|---|---|---|---|---|---|
| | peak 1 | | peak 2 | | peak 3 | | | |
| | MHz | dB | MHz | dB | MHz | dB | MHz | dB |
| Embodiment example 1 | 5.2 | −2.0 | 14.8 | 1.2 | — | — | 12.3 | −0.4 |
| Embodiment example 2 | 7.2 | −1.3 | 13.4 | 0.1 | 18.6 | −1.0 | 12.3 | −0.5 |
| Comparison example 1 | 9.8 | −0.4 | — | — | — | — | 12.3 | −1.0 |
| Comparison example 2 | 3.4 | −2.2 | — | — | — | — | 12.3 | −2.3 |
| Embodiment example 3 | 5.2 | −2.0 | 14.8 | 1.2 | — | — | 12.3 | −0.4 |
| Embodiment example 4 | 7.2 | −1.3 | 13.4 | 0.1 | 18.6 | −1.0 | 12.3 | −0.5 |
| Embodiment example 5 | 5.8 | 3.8 | 13.2 | 2.0 | 19.2 | 1.4 | 12.3 | 1.1 |
| Embodiment example 6 | | | | | | | | |
| Embodiment example 7 | | | | | | | | |

TABLE 1-continued

| | | | | | | | | |
|---|---|---|---|---|---|---|---|---|
| Embodiment example 8 | 5.6 | 2.2 | 13.2 | 3.7 | 19.2 | 3.1 | 12.3 | 3.1 |
| Embodiment example 9 | 6.2 | 5.0 | 13.2 | 3.7 | 20.2 | −0.1 | 12.3 | 2.9 |
| Comparison example 3 | 4.2 | 7.0 | — | — | — | — | 12.3 | −25.6 |
| Comparison example 4 | 3.4 | −2.2 | — | — | — | — | 12.3 | −2.3 |

| | | image quality evaluation result | | | | | | |
|---|---|---|---|---|---|---|---|---|
| | display mode | distance resplution (μm) | azimuth resolution (μm) | penetration (mm) | wrist | metacarpo phalangeal joint flexor tendon | long head of biceps brachii tendon | medial meniscu |
| Embodiment example 1 | fundamental wave | 308 | 677 | 59 | 8.2 | 8.4 | 7.3 | 7.0 |
| Embodiment example 2 | | 312 | 660 | 65 | 8.6 | 8.8 | 7.8 | 7.3 |
| Comparison example 1 | | 456 | 630 | 42 | 6.4 | 7.0 | 5.9 | 4.8 |
| Comparison example 2 | | 315 | 655 | 57 | 8.2 | 8.5 | 7.7 | 7.1 |
| Embodiment example 3 | THI | 285 | 645 | 54 | 8.9 | 8.9 | 7.8 | 7.6 |
| Embodiment example 4 | | 240 | 632 | 55 | 9.4 | 9.6 | 8.4 | 8.0 |
| Embodiment example 5 | | 225 | 651 | 59 | 9.6 | 9.7 | 8.8 | 8.2 |
| Embodiment example 6 | | 278 | 643 | 53 | 9.0 | 9.0 | 8.0 | 7.6 |
| Embodiment example 7 | | 341 | 638 | 47 | 7.7 | 7.4 | 7.5 | 7.0 |
| Embodiment example 8 | | 299 | 662 | 53 | 8.6 | 8.8 | 8.4 | 7.7 |
| Embodiment example 9 | | 330 | 668 | 54 | 8.2 | 8.3 | 8.0 | 7.5 |
| Comparison example 3 | | 512 | 598 | 40 | 5.6 | 5.9 | 5.2 | 5.0 |
| Comparison example 4 | | 320 | 680 | 48 | 8.1 | 8.0 | 7.3 | 6.6 |

<Evaluation Results>

From the results shown in Table 1, it is understood that Embodiment examples 1 to 9 exhibit good distance resolution and greater penetration comparing to Comparison examples 1 and 3 where ultrasound transmission and reception is performed with pulse signals of the drive waveforms 3 and 8, respectively. Further, with respect to Embodiment examples 1 to 9, their visualization evaluations of a wrist, a metacarpo phalangeal joint flexor tendon, a long head of biceps brachii tendon and a medial meniscu are higher comparing to Comparison examples 1 and 3.

In a case where ultrasound transmission and reception is performed with a pulse signal of the drive waveform 4, although Comparison examples 2 and 4 do not exhibit specific inferiority in their ultrasound images based on fundamental waves, in terms of ultrasound images obtained based on THI, their visualization evaluations, especially in a medial meniscu, are low comparing to Embodiment examples 3 to 9.

As described above, in the embodiment, the ultrasound probe 2 outputs transmission ultrasound toward a subject by a pulse signal being input and outputs received signals by receiving reflected ultrasound from the subject. The transmission unit 12 outputs a pulse signal of a drive waveform formed of rectangular waves to make the ultrasound probe 2 generate transmission ultrasound. With respect to the frequency power spectrum of the pulse signal, there are intensity peaks in a frequency band included in the transmission frequency band at −20 dB of the ultrasound probe 2 on the low frequency side and the high frequency side of the center frequency in the transmission frequency band, and also, intensities in the frequency regions between the plurality of intensity peaks are −20 dB or greater with the maximum intensity value among the intensity peaks being the reference. As a result, there is no need to add a complicated circuit for forming a waveform of a pulse signal, and high resolution can be maintained in transmission ultrasound at low cost. Further, with respect to an ultrasound image based on fundamental waves, since an ultrasound waveform of high amplitude and short pulses can be obtained, penetration can be improved by the low frequency component being increased while maintaining high resolution.

Moreover, according to the embodiment, the transmission unit 12 outputs pulse signals having different drive waveforms for a plurality of times on the same scanning line with time intervals therebetween. The image generation unit 14 combines the received signals each of which obtained from reflected ultrasound of the transmission ultrasound generated by each output of pulse signal, and generates ultrasound image data on the basis of the composite pulse signal. As a result, since a harmonic can be received in a broadband by pulse inversion, an ultrasound image in which resolution is even more improved can be obtained at a low cost.

Further, according to the embodiment, in the frequency power spectrum of the pulse signal, the intensity of the frequency component at at least any one of the plurality of intensity peaks is greater than the intensity of the frequency component at the frequency same as the center frequency in the transmission frequency band at −20 dB of the ultrasound probe 2. As a result, ultrasound can be transmitted in a bandwidth broader than the transmission bandwidth of the ultrasound probe and the resolution can be improved.

Furthermore, according to the embodiment, in the frequency power spectrum of a pulse signal, there are two or more intensity peaks on the high frequency side of the center frequency in the transmission frequency band at −20 dB of the ultrasound probe 2, the intensity peaks being included in the transmission frequency band. As a result, ultrasound having broader bandwidth on the high frequency side can be transmitted and the resolution can be improved.

Moreover, according to the embodiment, since a pulse signal is formed of rectangular waves of five values or less, resolution can be improved at a low cost.

Further, according to the embodiment, since the fractional bandwidth at −20 dB is 110% or greater in the ultrasound probe 2, ultrasound of even higher resolution can be transmitted.

The Description of the embodiment of the present invention is merely an example of an ultrasound diagnostic imaging apparatus according to the present invention and the present invention is not limited to what is described. The detail configuration and detail operations of the functional parts which constitute the ultrasound diagnostic imaging apparatus can be modified arbitrarily.

The entire disclosure of Japanese Patent Application No. 2013-041380 filed on Mar. 4, 2013 is incorporated herein by reference in its entirety.

What is claimed is:

1. An ultrasound diagnostic apparatus, comprising:
  an ultrasound probe which outputs transmission ultrasound corresponding to a drive signal, and which receives reflected ultrasound from a subject;
  a transmission circuit which outputs the drive signal to the ultrasound probe;
  a hardware processor which controls the transmission circuit to output, as the drive signal, a first drive signal having a first drive waveform and a second drive signal having a second drive waveform that is different from the first drive waveform; and
  a reception circuit which generates a first signal based on the reflected ultrasound corresponding to the transmission ultrasound that is output based on the first drive signal having the first drive waveform and a second signal based on the reflected ultrasound corresponding to the transmission ultrasound that is output based on the second drive signal having the second drive waveform;
  wherein:
    the hardware processor is configured to perform control to extract a harmonic signal component used to generate an image by adding the first signal and the second signal and filtering the added first signal and second signal to thereby extract the harmonic signal component, and
    the hardware processor is configured to control the transmission circuit so that (i) frequency spectrums of the first drive signal and the second drive signal have, in a frequency band included in a transmission frequency band at −20 dB of the ultrasound probe, a first intensity peak on a low frequency side of a center frequency of the transmission frequency band and which is an intensity peak on a lowest frequency side among intensity peaks included in the transmission frequency band, and a second intensity peak on a high frequency side of the center frequency and which is an intensity peak on a highest frequency side among the intensity peaks included in the transmission frequency band, and (ii) an intensity of an entire frequency region between the first intensity peak and the second intensity peak is −20 dB or greater relative to a maximum intensity value from among intensity values of the intensity peaks included in the transmission frequency band.

2. The ultrasound diagnostic apparatus of claim 1, wherein the transmission ultrasound which is output based on the first drive signal and the transmission ultrasound which is output based on the second drive signal are output on a same scanning line with a time interval therebetween.

3. The ultrasound diagnostic apparatus of claim 1, wherein the hardware processor is configured to control the transmission circuit so that, in the frequency spectrums of the first and second drive signals, each of the first intensity peak and the second intensity peak is greater than an intensity of a frequency component at as the center frequency in the transmission frequency band at −20 dB of the ultrasound probe.

4. The ultrasound diagnostic apparatus of claim 1, wherein a fractional bandwidth at −20 dB is 110% or greater in the ultrasound probe.

5. The ultrasound diagnostic apparatus of claim 1, wherein the second drive signal has polarity which is the inverse of polarity of the first drive signal.

6. The ultrasound diagnostic apparatus of claim 1, wherein each of the first drive signal and the second drive signal is a pulse signal.

* * * * *